(12) United States Patent
Achard et al.

(10) Patent No.: US 6,566,356 B2
(45) Date of Patent: May 20, 2003

(54) PHARMACEUTICAL COMPOSITIONS CONTAINING 3-AMINOAZETIDINE DERIVATIVES, NOVEL DERIVATIVES AND THEIR PREPARATION

(75) Inventors: Daniel Achard, Thiais (FR); Hervé Bouchard, Thiais (FR); Jean Bouquerel, Drancy (FR); Bruno Filoche, Creteil (FR); Serge Grisoni, Choisy le Roi (FR); Augustin Hittinger, Igny (FR); Michael R. Myers, Saint Nom la Breteche (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 09/798,589

(22) Filed: Mar. 2, 2001

(65) Prior Publication Data
US 2002/0019383 A1 Feb. 14, 2002

Related U.S. Application Data
(60) Provisional application No. 60/200,098, filed on Apr. 27, 2000.

(30) Foreign Application Priority Data
Mar. 3, 2000 (FR) .............................. 00 02777

(51) Int. Cl.⁷ .................. C07D 403/02; C07D 401/02; A61K 31/498
(52) U.S. Cl. ............................ 514/210.01; 514/210.19; 514/210.2; 514/210.21; 544/335; 546/172; 546/268.1; 548/314.7; 548/518; 548/953
(58) Field of Search ............................ 548/314.7, 953, 548/518; 546/172, 268.1; 544/335; 514/210.01, 210.19, 210.2, 210.21

(56) References Cited

U.S. PATENT DOCUMENTS
4,242,261 A 12/1980 Cale, Jr. .................. 260/239 A

FOREIGN PATENT DOCUMENTS
| EP | 0406112 | 12/1994 |
| WO | 9701556 | 1/1997 |
| WO | 9901451 | 1/1999 |
| WO | WO 99/01451 | * 1/1999 |

* cited by examiner

Primary Examiner—Deepak Rao
(74) Attorney, Agent, or Firm—Irving Newman

(57) ABSTRACT

The present invention relates to pharmaceutical compositions containing, as active ingredient, a compound of formula:

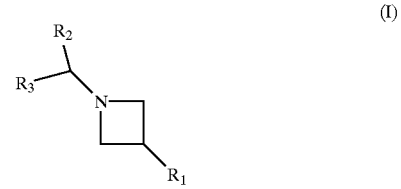

(I)

in which $R_1$ represents a radical —NHCOR$_4$ or —N(R$_5$)—Y—R$_6$, Y is CO or SO$_2$, $R_4$ represents a radical -alk-SO$_2$—R$_{11}$, -alk-SO$_2$—CH═CH—R$_{11}$ or Het substituted with —SO$_2$—R$_{11}$ or a phenyl radical substituted with —SO$_2$—R$_{11}$ or -alk-SO$_2$—R$_{11}$, $R_5$ represents a hydrogen atom or an alkyl radical, $R_6$ represents a phenylalkyl, Het or Ar radical, to the novel derivatives of formula (I) and to their preparation.

18 Claims, No Drawings

PHARMACEUTICAL COMPOSITIONS CONTAINING 3-AMINOAZETIDINE DERIVATIVES, NOVEL DERIVATIVES AND THEIR PREPARATION

This application claims the benefit of U.S. Provisional Application No. 60/200,098, filed Apr. 27, 2000.

The present invention relates to pharmaceutical compositions containing, as active ingredient, at least one compound of formula:

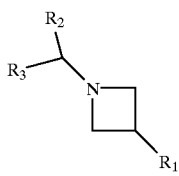

(I)

or one of its pharmaceutically acceptable salts, to the novel derivatives of formula (I), to their pharmaceutically acceptable salts and to their preparation.

The compound of formula (I) for which $R_2$ and $R_3$ represent phenyl radicals, $R_1$ represents a radical —$N(R_5)$—Y—$R_6$, Y is $SO_2$, $R_5$ represents a methyl radical and $R_6$ represents a phenyl radical is described as a synthesis intermediate in Patent WO 99/01451. The other compounds and their pharmaceutically acceptable salts are novel and as such form parts of the invention.

In formula (I)

$R_1$ represents a radical —$NHCOR_4$ or —$N(R_5)$—Y—$R_6$,

Y is CO or $SO_2$, $R_2$ and $R_3$, which are identical or different, represent either an aromatic selected from phenyl, naphthyl and indenyl, these aromatics being unsubstituted or substituted with one or more halogen atoms or alkyl, alkoxy, formyl, hydroxyl, trifluoromethyl, trifluoromethoxy, —CO-alk, cyano, —COOH, —COOalk, —$CONR_7R_8$, —CO—NH—$NR_9R_{10}$, alkylsulfanyl, alkylsulfinyl, alkylsulfonyl, alkylsulfanylalkyl, alkylsulfinylalkyl, alkylsulfonylalkyl, hydroxyalkyl or -alk-$NR_7R_8$ radicals; or a heteroaromatic selected from benzofuryl, benzothiazolyl, benzothienyl, benzoxazolyl, chromanyl, 2,3-dihydrobenzofuryl, 2,3-dihydrobenzothienyl, pyrimidinyl, furyl, imidazolyl, isochromanyl, isoquinolyl, pyrrolyl, pyridyl, quinolyl, 1,2,3,4-tetrahydro-isoquinolyl, thiazolyl and thienyl rings, it being possible for these heteroaromatics to be unsubstituted or substituted with a halogen atom or an alkyl, alkoxy, hydroxyl, trifluoromethyl, trifluoromethoxy, cyano, —COOH, —COOalk, —CO—NH—$NR_9R_{10}$, —$CONR_7R_8$, -alk-$NR_9R_{10}$, alkylsulfanyl, alkylsulfinyl, alkylsulfonyl, alkylsulfanylalkyl, alkylsulfinylalkyl, alkylsulfonylalkyl or hydroxyalkyl radical, $R_4$ represents a radical -alk-$SO_2$—$R_{11}$, -alk-$SO_2$—CH=CH—$R_{11}$, Het substituted with —$SO_2$—$R_{11}$ or phenyl substituted with —$SO_2$—$R_{11}$ or -alk-$SO_2$—$R_{11}$, $R_5$ represents a hydrogen atom or an alkyl radical, $R_6$ represents a phenylalkyl, Het or Ar radical, $R_7$ and $R_8$, which are identical or different, represent a hydrogen atom or an alkyl radical or alternatively $R_7$ and $R_8$ together form with the nitrogen atom to which they are attached a 3- to 10-membered saturated mono- or bicyclic heterocycle, optionally containing another heteroatom selected from oxygen, sulfur and nitrogen and being optionally substituted with one or more alkyl radicals, $R_9$ and $R_{10}$, which are identical or different, represent a hydrogen atom or an alkyl, —COOalk, cycloalkyl, alkylcycloalkyl, -alk-O-alk or hydroxyalkyl radical or alternatively $R_9$ and $R_{10}$ together form with the nitrogen atom to which they are attached a 3- to 10-membered saturated or unsaturated mono- or bicyclic heterocycle, optionally containing another heteroatom selected from oxygen, sulfur and nitrogen and being optionally substituted with one or more alkyl, —COalk, —COOalk, —CO—NHalk, —CS—NHalk, oxo, hydroxyalkyl, -alk-O-alk or —CO—$NH_2$ radicals, $R_{11}$ represents an alkyl, Ar or Het radical, Ar represents a phenyl, naphthyl or indenyl radical, these radicals being optionally substituted with one or more halogen atoms or alkyl, alkoxy, cyano, —CO-alk, —COOH, —COOalk, —$CONR_{12}R_{13}$, —CO—NH—$NR_{14}R_{15}$, alkylsulfanyl, alkylsulfinyl, alkylsulfonyl, -alk-$NR_{14}R_{15}$, —$NR_{14}R_{15}$, alkylthioalkyl, formyl, hydroxyl, hydroxyalkyl, Het, —O-alk-NH-cycloalkyl, $OCF_3$, $CF_3$, —NH—CO-alk, —$SO_2NH_2$, —NH—$COCH_3$, —NH—COOalk or Het radicals, or alternatively, on 2 adjacent carbon atoms, with a dioxymethylene, Het represents a 3- to 10-membered unsaturated or saturated mono- or bicyclic heterocycle containing one or more heteroatoms selected from oxygen, sulfur and nitrogen optionally substituted with one or more halogen atoms or alkyl, alkoxy, vinyl, alkoxycarbonyl, oxo, hydroxyl, $OCF_3$ or $CF_3$ radicals, the nitrogen-containing heterocycles being optionally in their N-oxidized form, $R_{12}$ and $R_{13}$, which are identical or different, represent a hydrogen atom or an alkyl radical or alternatively $R_{12}$ and $R_{13}$ together form with the nitrogen atom to which they are attached a 3- to 10-membered saturated mono- or bicyclic heterocycle, optionally containing another heteroatom selected from oxygen, sulfur and nitrogen and being optionally substituted with one or more alkyl radicals, $R_{14}$ and $R_{15}$, which are identical or different, represent a hydrogen atom or an alkyl, —COOalk, cycloalkyl, alkylcycloalkyl, -alk-O-alk or hydroxyalkyl radical or alternatively $R_{14}$ and $R_{15}$ together form with the nitrogen atom to which they are attached a 3- to 10-membered saturated or unsaturated mono- or bicyclic heterocycle, optionally containing another heteroatom selected from oxygen, sulfur and nitrogen and being optionally substituted with one or more alkyl, —COalk, —COOalk, —CO—NHalk, —CS—NHalk, oxo, hydroxyalkyl, -alk-O-alk or —CO—$NH_2$ radicals, alk represents an alkyl or alkylene radical.

In the preceding definitions and in those which follow, unless otherwise stated, the alkyl and alkylene radicals and portions and the alkoxy radicals and portions are in the form of a straight or branched chain and contain 1 to 6 carbon atoms and the cycloalkyl radicals contain 3 to 10 carbon atoms.

Among the alkyl radicals, there may be mentioned the methyl, ethyl, n-propyl, isopropyl, n-butyl, sec-butyl, isobutyl, tert-butyl, pentyl and hexyl radicals. Among the alkoxy radicals, there may be mentioned the methoxy, ethoxy, n-propoxy, iso-propoxy, n-butoxy, iso-butoxy, sec-butoxy, tert-butoxy and pentyloxy radicals.

Among the cycloalkyl radicals, there may be mentioned the cyclopropyl, cyclobutyl, cyclopentyl and cyclohexyl radicals.

The term halogen comprises chlorine, fluorine, bromine and iodine.

Among the heterocycles represented by Het, the following heterocycles may be mentioned: benzimidazole, benzoxazole, benzothiazole, benzothiophene, cinnoline, thiophene, quinazoline, quinoxaline, quinoline, pyrazole, pyrrole, pyridine, imidazole, indole, isoquinoline, pyrimidine, thiazole, thiadiazole, piperidine, piperazine, pyrrolidine, triazole, furan, tetrahydroisoquinoline, tetrahydroquinoline, these heterocycles being optionally substituted with one or more halogen atoms or alkyl, alkoxy, vinyl, alkoxycarbonyl, oxo, hydroxyl, $OCF_3$ or $CF_3$ radicals.

The compounds of formula (I) may be provided in the form of enantiomers and of diastereoisomers. These optical isomers and mixtures thereof also form part of the invention.

Preferably, the compounds of formula (I) are those for which $R_1$ represents a radical —N($R_5$)—Y—$R_6$, Y is $SO_2$, $R_2$ represents either a phenyl which is unsubstituted or substituted with one or more halogen atoms or alkyl, alkoxy, trifluoromethyl, trifluoromethoxy, cyano, —CON$R_7R_8$, hydroxyalkyl or -alk-N$R_7R_8$ radicals; or a heteroaromatic selected from the pyridyl, pyrimidyl, thiazolyl and thienyl rings, it being possible for these heteroaromatics to be unsubstituted or substituted with a halogen atom or an alkyl, alkoxy, hydroxyl, trifluoromethyl, trifluoromethoxy, —CON$R_7R_8$, -alk-N$R_9R_{10}$, alkylsulfanyl, alkylsulfinyl, alkylsulfonyl or hydroxyalkyl radical, $R_3$ represents either a phenyl which is unsubstituted or substituted with one or more halogen atoms or alkyl, alkoxy, trifluoromethyl, trifluoromethoxy, cyano, —CON$R_7R_8$, hydroxyalkyl or -alk-N$R_7R_8$ radicals; or a heteroaromatic selected from the pyridyl, pyrimidyl, thiazolyl and thienyl rings, it being possible for these heteroaromatics to be unsubstituted or substituted with a halogen atom or an alkyl, alkoxy, hydroxyl, trifluoromethyl, trifluoromethoxy, —CON$R_7R_8$, -alk-N$R_9R_{10}$, alkylsulfanyl, alkylsulfinyl, alkylsulfonyl or hydroxyalkyl radical, $R_5$ represents a hydrogen atom or an alkyl radical, $R_6$ represents a naphthyl, phenylalkyl, Het or phenyl radical optionally substituted with one or more halogen atoms or alkyl, alkoxy, cyano, —CO-alk, COOalk, —CON$R_{12}R_{13}$, -alk-N$R_{14}R_{15}$, —N$R_{14}R_{15}$, hydroxyl, hydroxyalkyl, Het, $OCF_3$, $CF_3$, —NH—CO-alk, —$SO_2NH_2$ or —NH—COOalk radicals, or alternatively, on 2 adjacent carbon atoms, with dioxymethylene, $R_7$ and $R_8$, which are identical or different, represent a hydrogen atom or an alkyl radical or alternatively $R_7$ and $R_8$ together form with the nitrogen atom to which they are attached a 3- to 10-membered saturated mono- or bicyclic heterocycle, optionally containing another heteroatom selected from oxygen, sulfur and nitrogen and being optionally substituted with one or more alkyl radicals, $R_9$ and $R_{10}$, which are identical or different, represent a hydrogen atom or an alkyl, cycloalkyl, alkylcycloalkyl or hydroxyalkyl radical or alternatively $R_9$ and $R_{10}$ together form with the nitrogen atom to which they are attached a 3- to 10-membered saturated or unsaturated mono- or bicyclic heterocycle, optionally containing another heteroatom selected from oxygen, sulfur and nitrogen and being optionally substituted with one or more alkyl, oxo or —CO—$NH_2$ radicals, $R_{12}$ and $R_{13}$, which are identical or different, represent a hydrogen atom or an alkyl radical or alternatively $R_{12}$ and $R_{13}$ together form with the nitrogen atom to which they are attached a 3- to 10-membered saturated mono- or bicyclic heterocycle, optionally containing another heteroatom selected from oxygen, sulfur and nitrogen and being optionally substituted with one or more alkyl radicals, $R_{14}$ and $R_{15}$, which are identical or different, represent a hydrogen atom or an alkyl, cycloalkyl, alkylcycloalkyl or hydroxyalkyl radical or alternatively $R_{14}$ and $R_{15}$ together form with the nitrogen atom to which they are attached a 3- to 10-membered saturated or unsaturated mono- or bicyclic heterocycle, optionally containing another heteroatom selected from oxygen, sulfur and nitrogen and being optionally substituted with one or more alkyl, oxo, hydroxyalkyl or —CO—$NH_2$ radicals, Het represents a 3- to 10-membered unsaturated or saturated mono- or bicyclic heterocycle containing one or more heteroatoms selected from oxygen, sulfur and nitrogen optionally substituted with one or more halogen atoms or alkyl, alkoxy, vinyl, alkoxycarbonyl, oxo or hydroxyl radicals, the nitrogen-containing heterocycles being optionally in their N-oxidized form and, preferably, Het represents a heterocycle selected from the following heterocycles: benzimidazole, benzoxazole, benzothiazole, benzothiophene, thiophene, quinazoline, quinoxaline, quinoline, pyrrole, pyridine, imidazole, indole, isoquinoline, pyrimidine, thiazole, thiadiazole, furan, tetrahydroisoquinoline and tetrahydroquinoline, these heterocycles being optionally substituted with one or more halogen atoms or alkyl, alkoxy, vinyl, oxo, hydroxyl, $OCF_3$ or $CF_3$ radicals.

Still more preferably, the compounds of formula (I) are selected from the following compounds:

$R_1$ represents a radical —N($R_5$)—Y—$R_6$,

Y is $SO_2$, $R_2$ represents either a phenyl which is unsubstituted or substituted with one or more halogen atoms or alkyl, alkoxy, trifluoromethyl, trifluoromethoxy or hydroxyalkyl radicals; or a heteroaromatic selected from pyridyl and pyrimidyl rings, it being possible for these heteroaromatics to be unsubstituted or substituted with a halogen atom or an alkyl, alkoxy, hydroxyl, trifluoromethyl or trifluoromethoxy radical, $R_3$ represents either a phenyl which is unsubstituted or substituted with one or more halogen atoms or alkyl, alkoxy, trifluoromethyl, trifluoromethoxy or hydroxyalkyl radicals; or a heteroaromatic selected from pyridyl and pyrimidyl rings, it being possible for these heteroaromatics to be unsubstituted or substituted with a halogen atom or an alkyl, alkoxy, hydroxyl, trifluoromethyl or trifluoromethoxy radical, $R_5$ represents a hydrogen atom or an alkyl radical, $R_6$ represents a naphthyl, phenylalkyl, Het or phenyl radical optionally substituted with one or more halogen atoms or alkyl, alkoxy, —N$R_{14}R_{15}$, hydroxyl, hydroxyalkyl, $OCF_3$, $CF_3$ or —$SO_2NH_2$ radicals, or alternatively, on 2 adjacent carbon atoms, with dioxymethylene, $R_{14}$ and $R_{15}$, which are identical or different, represent a hydrogen atom or an alkyl, cycloalkyl, alkylcycloalkyl or hydroxyalkyl radical or alternatively $R_{14}$ and $R_{15}$ together form with the nitrogen atom to which they are attached a 3- to 10-membered saturated or unsaturated mono- or bicyclic heterocycle, optionally containing another heteroatom selected from oxygen, sulfur and nitrogen and being optionally substituted with one or more alkyl, oxo, hydroxyalkyl or —CO—$NH_2$ radicals, Het represents a 3- to 10-membered unsaturated or saturated mono- or bicyclic heterocycle containing one or more heteroatoms selected from oxygen, sulfur and nitrogen optionally substituted with one or more halogen atoms or alkyl, alkoxy, vinyl, alkoxycarbonyl, oxo or hydroxyl radicals, the nitrogen-containing heterocycles being optionally in their N-oxidized form and, preferably, Het represents a heterocycle selected from the following heterocycles: benzimidazole, benzoxazole, benzothiazole, benzothiophene, thiophene, quinoline, pyrrole, pyridine, pyrimidine, thiazole, thiadiazole, furan, tetrahydroisoquinoline and tetrahydroquinoline, these heterocycles being optionally substituted with one or more halogen atoms or alkyl, alkoxy, vinyl, oxo, hydroxyl, $OCF_3$ or $CF_3$ radicals.

The compounds of formula (I) for which $R_1$ represents a radical —$NHCOR_4$ may be prepared according to the following reaction scheme:

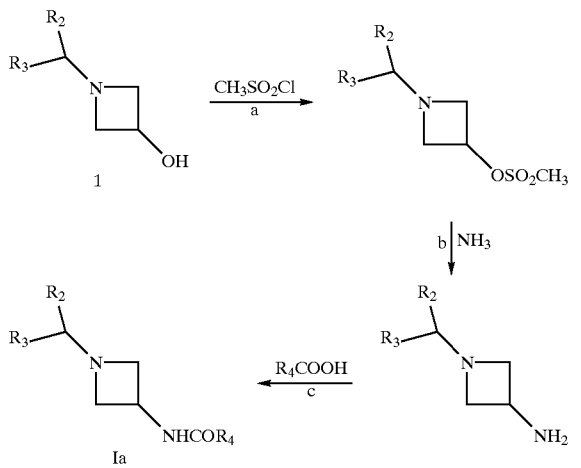

In these formulae, $R_2$, $R_3$ and $R_4$ have the same meanings as in formula (I).

Step a is generally carried out in an inert solvent such as tetrahydrofuran, dioxane, a chlorinated solvent (for example dichloromethane or chloroform), at a temperature of between 15 and 30° C., in the presence of a base such as a trialkylamine (for example triethylamine or dipropylethylamine) or in pyridine, at a temperature of between 0 and 30° C.

Step b is preferably carried out in methanol, in an autoclave, at a temperature of between 50 and 70° C.

Step c is generally carried out in the presence of a condensing agent used in peptide chemistry, such as a carbodiimide (for example 1-(3-dimethylamiopropyl)-3-ethylcarbodiimide or N,N'-dicyclohexylcarbodiimide) or N,N'carbonyldiimidazole, in an inert solvent such as an ether (for example tetrahydrofuran or dioxane), an amide (dimethylformamide) or a chlorinated solvent (for example methylene chloride, 1,2-dichloroethane or chloroform) at a temperature of between 0° C. and the boiling point of the reaction mixture. It is also possible to use a reactive derivative of the acid such as an acid chloride, optionally in the presence of an acid acceptor such as a nitrogen-containing organic base (for example trialkylamine, pyridine, 1,8-diazabicyclo[5.4.0]undec-7-ene or 1,5-diazabicyclo[4.3.0]-non-5-ene), in a solvent as cited above, or a mixture of these solvents, at a temperature of between 0° C. and the boiling point of the reaction mixture.

The derivatives $R_4COOH$ are commercially available or may be obtained according to the methods described in R. C. LAROCK, Comprehensive Organic Transformations, VCH editor.

The azetidinols of formula 1 may be obtained by application or adaptation of the methods described by KATRITZKY A. R. et al., J. Heterocycl. Chem., 271 (1994) or DAVE P. R., J. Org. Chem., 61, 5453 (1996) and in the examples. The procedure is generally carried out according to the following reaction scheme:

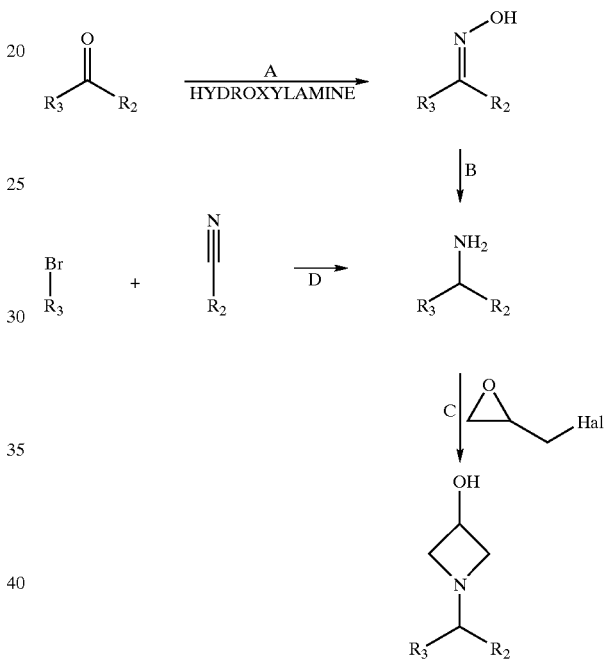

in these formulae, $R_2$ and $R_3$ have the same meanings as in formula (I) and Hal represents a chlorine or bromine atom.

In step A, the procedure is preferably carried out in an inert solvent such as a 1–4C aliphatic alcohol (for example ethanol or methanol), optionally in the presence of an alkali metal hydroxide, at the boiling point of the reaction medium.

In step B, the reduction is generally carried out by means of lithium aluminum hydride, in tetrahydrofuran at the boiling point of the reaction medium.

In step C, the procedure is preferably carried out in an inert solvent such as a 1–4C aliphatic alcohol (for example ethanol or methanol), in the presence of sodium hydrogen carbonate, at a temperature of between 20° C. and the boiling point of the reaction medium.

In step D, the procedure is carried out according to the method described by GRISAR M. et al. in J. Med. Chem., 885 (1973). The magnesium compound of the brominated derivative is formed and then the nitrile is caused to react, in an ether such as ethyl ether, at a temperature of between 0° C. and the boiling point of the reaction medium. After hydrolysis with an alcohol, the intermediate imine is reduced in situ with sodium borohydride at a temperature of between 0° C. and the boiling point of the reaction medium.

The derivatives $R_2$—CO—$R_3$ are commercially available or may be obtained by application or adaptation of the methods described by KUNDER N. G. et al. J. Chem. Soc. Perkin Trans 1, 2815 (1997); MORENO-MARRAS M., Eur. J. Med. Chem., 23 (5) 477 (1988); SKINNER et al., J. Med. Chem., 14 (6) 546 (1971); HURN N. K., Tet. Lett., 36 (52) 9453 (1995); MEDICI A. et al., Tet. Lett., 24 (28) 2901 (1983); RIECKE R. D. et al., J. Org. Chem., 62 (20) 6921 (1997); KNABE J. et al., Arch. Pharm., 306 (9) 648 (1973); CONSONNI R. et al., J. Chem. Soc. Perkin Trans 1, 1809 (1996); FR-96-2481 and JP-94-261393.

The derivatives $R_3Br$ are commercially available or may be obtained by application or adaptation of the methods described by BRANDSMA L. et al., Synth. Comm., 20 (11) 1697 and 3153 (1990); LEMAIRE M. et al., Synth. Comm., 24 (1) 95 (1994); GODA H. et al., Synthesis, 9 849 (1992); BAEUERLE P. et al., J. Chem. Soc. Perkin Trans 2, 489 (1993).

The derivatives $R_2CN$ are commercially available or may be obtained by application or adaptation of the methods described by BOUYSSOU P. et al., J. Het. Chem., 29 (4) 895 (1992); SUZUKI N. et al., J. Chem. Soc. Chem. Comm., 1523 (1984); MARBURG S. et al., J. Het. Chem., 17 1333 (1980); PERCEC V. et al., J. Org. Chem., 60 (21) 6895 (1995).

The compounds of formula (I) for which $R_1$ represents a radical —$N(R_5)$—Y—$R_6$ may be prepared according to the following reaction scheme:

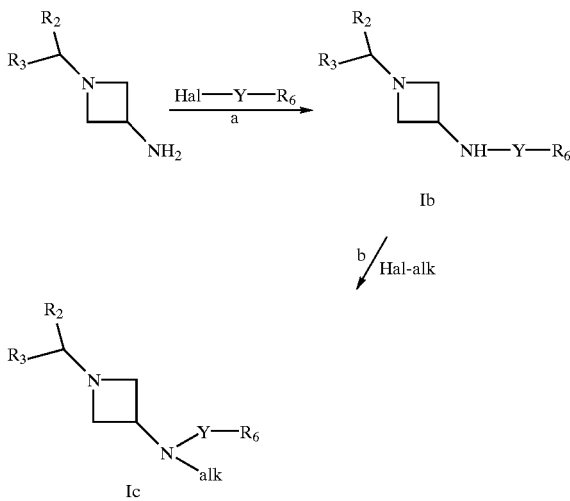

in these formulae, Y, $R_2$, $R_3$ and $R_6$ have the same meanings as in formula (I), Hal represents a halogen atom and, preferably, an iodine, chlorine or bromine atom.

Step a is generally carried out in an inert solvent such as tetrahydrofuran, dioxane or a chlorinated solvent (for example dichloromethane or chloroform), in the presence of an amine such as a trialkylamine (for example triethylamine), at a temperature of between 5° C. and 20° C.

Step b is generally carried out in an inert solvent such as tetrahydrofuran, in the presence of sodium hydride, at a temperature of 0° C. and the boiling point of the reaction medium.

The Hal-$SO_2R_6$ derivatives are commercially available or may be obtained by halogenation of the corresponding sulfonic acids, in particular in situ in the presence of chlorosulfonyl isocyanate and alcohol, in a halogenated solvent (for example dichloromethane or chloroform).

The Hal-CO—$R_6$ derivatives are commercially available or may be prepared according to the methods described in R. C. LAROCK, Comprehensive Organic Transformations, VCH editor.

The compounds of formula (I) may also be prepared according to the following reaction scheme:

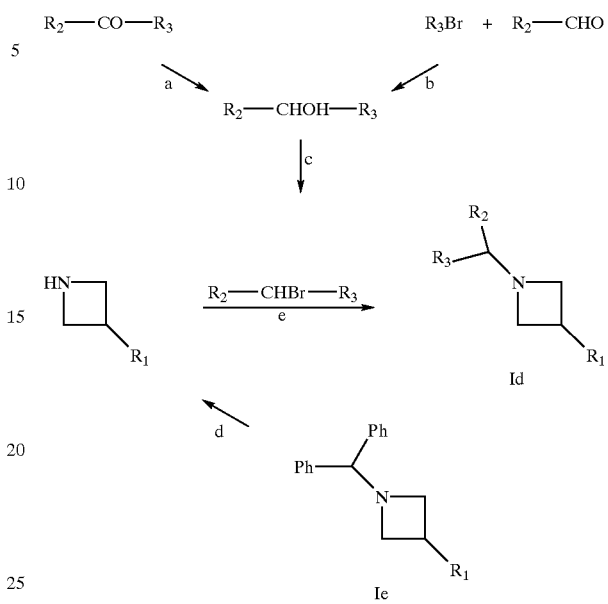

In these formulae, $R_1$, $R_2$ and $R_3$ have the same meanings as in formula (I) and Ph represents a phenyl.

Step a is generally carried out in an alcohol such as methanol, in the presence of sodium borohydride, at a temperature in the region of 20° C.

In step b, the magnesium compound of the brominated derivative is prepared and it is caused to react, in an inert solvent such as ethyl ether or tetrahydrofuran, at a temperature of between 0° C. and the boiling point of the reaction medium.

Step c is carried out by means of a halogenating agent such as hydrobromic acid, thionyl bromide, thionyl chloride, a mixture of triphenylphosphine and carbon tetrabromide or tetrachloride, in acetic acid or an inert solvent such as dichloromethane, chloroform, carbon tetrachloride or toluene, at a temperature of between 0° C. and the boiling point of the reaction medium.

Step d is carried out by means of hydrogen, in the presence of palladized charcoal, in an alcohol such as methanol, at a temperature in the region of 20° C.

Step e is carried out in an inert solvent such as acetonitrile, in the presence of an alkali metal carbonate (for example potassium carbonate) and potassium iodide, at a temperature of between 20° C. and the boiling point of the reaction medium.

The derivatives $R_3Br$ and the derivatives $R_2$—CHO are commercially available or may be obtained according to the methods described for example by R. C. LAROCK, Comprehensive Organic Transformations, VCH editor.

The compounds of formula (I) for which $R_1$ represents a radical —$N(R_5)$—Y—$R_6$ in which $R_6$ is a phenyl radical substituted with a hydroxyl radical may also be prepared by hydrolysis of a corresponding compound of formula (I) for which $R_1$ represents a radical —$N(R_5)$—Y—$R_6$ in which $R_6$ is a phenyl radical substituted with an alkoxy radical.

This hydrolysis is generally carried out in an inert solvent such as a chlorinated solvent (for example dichloromethane or chloroform), by means of boron tribromide, at a temperature in the region of 20° C.

The compounds of formula (I) for which $R_1$ represents a radical —$N(R_5)$—Y—$R_6$ in which $R_6$ is a phenyl radical substituted with a hydroxy(1C)alkyl radical may also be prepared by the action of diisobutylaluminum hydride on a corresponding compound of formula (I) for which $R_1$ represents a radical —N($R_5$)—Y—$R_6$ in which $R_6$ is a phenyl radical substituted with an alkoxycarbonyl radical.

This reaction is generally carried out in an inert solvent such as toluene, by means of diisopropyl-aluminum hydride, at a temperature of between −50° C. and 25° C.

The compounds of formula (I) for which $R_1$ represents a radical —N($R_5$)—Y—$R_6$ in which $R_6$ is a phenyl radical substituted with a 1-pyrrolidinyl radical may also be prepared by the action of pyrrolidine and of a corresponding compound of formula (I) for which $R_1$ represents a radical —N($R_5$)—Y—$R_6$ in which $R_6$ is a phenyl radical substituted with a fluorine atom.

This reaction is preferably carried out in an inert solvent such as dimethyl sulfoxide, at a temperature of 90° C.

It is understood for persons skilled in the art that, to carry out the processes according to the invention which are described above, it may be necessary to introduce groups protecting amino, hydroxyl and carboxyl functions in order to avoid side reactions. These groups are those which allow removal without affecting the rest of the molecule. As examples of groups protecting the amino function, there may be mentioned tert-butyl or methyl carbamates which may be regenerated using iodotrimethylsilane or allyl using palladium catalysts. As examples of groups protecting the hydroxyl function, there may be mentioned triethylsilyl and tert-butyldimethylsilyl which may be regenerated using tetrabutylammonium fluoride or alternatively asymmetric acetals (methoxymethyl or tetrahydropyranyl for example) with regeneration using hydrochloric acid. As groups protecting carboxyl functions, there may be mentioned esters (allyl or benzyl for example), oxazoles and 2-alkyl-1,3-oxazolines. Other protecting groups which can be used are described by GREENE T. W. et al., Protecting Groups in Organic Synthesis, second edition, 1991, John Wiley & Sons.

The compounds of formula (I) may be purified by the customary known methods, for example by crystallization, chromatography or extraction.

The enantiomers of the compounds of formula (I) may be obtained by resolution of the racemates for example by chromatography on a chiral column according to PIRCKLE W. H. et al., Asymmetric synthesis, Vol. 1, Academic Press (1983) or by formation of salts or by synthesis from chiral precursors. The diastereoisomers may be prepared according to known conventional methods (crystallization, chromatography or from chiral precursors).

The compounds of formula (I) may be optionally converted to addition salts with an inorganic or organic acid by the action of such an acid in an organic solvent such as an alcohol, a ketone, an ether or a chlorinated solvent. These salts also form part of the invention.

As examples of pharmaceutically acceptable salts, the following salts may be mentioned: benzenesulfonate, hydrobromide, hydrochloride, citrate, ethanesulfonate, fumarate, gluconate, iodate, isethionate, maleate, methanesulfonate, methylene-bis-3-oxynaphthoate, nitrate, oxalate, pamoate, phosphate, salicylate, succinate, sulfate, tartrate, theophyllineacetate and p-toluenesulfonate.

The compounds of formula (I) exhibit advantageous pharmacological properties. These compounds possess a high affinity for the cannabinoid receptors and particularly those of the CB1 type. They are CB1-receptor antagonists and are therefore useful in the treatment and prevention of disorders affecting the central nervous system, the immune system, the cardiovascular or endocrine system, the respiratory system, the gastrointestinal apparatus and reproductive disorders (Hollister, Pharm. Rev.; 38, 1986, 1–20, Reny and Sinha, Prog. Drug Res., 36, 71–114 (1991), Consroe and Sandyk, in Marijuana/Cannabinoids, Neurobiology and Neurophysiology, 459, Murphy L. and Barthe A. Eds, CRC Press, 1992).

Accordingly, these compounds may be used for the treatment or prevention of psychoses including schizophrenia, anxiety disorders, depression, epilepsy, neurodegeneration, cerebellar and spinocerebellar disorders, cognitive disorders, cranial trauma, panic attacks, peripheral neuropathies, glaucomas, migraine, Parkinson's disease, Alzheimer's disease, Huntington's chorea, Raynaud's syndrome, tremor, obsessive-compulsive disorder, senile dementia, thymic disorders, Tourette's syndrome, tardive dyskinesia, bipolar disorders, cancers, movement disorders induced by medicaments, dystonia, endotoxemic shocks, hemorrhagic shocks, hypotension, insomnia, immunological diseases, multiple sclerosis, vomiting, asthma, appetite disorders (bulimia, anorexia), obesity, memory disorders, in weaning from chronic treatments and alcohol or drug abuse (opioids, barbiturates, cannabis, cocaine, amphetamine, phencyclide, hallucinogens, benzodiazepines for example), as analgesics or potentiators of the analgesic activity of the narcotic and nonnarcotic drugs. They may also be used for the treatment or prevention of intestinal transit.

The affinity of the compounds of formula (I) for the cannabis receptors has been determined according to the method described by KUSTER J. E., STEVENSON J. I., WARD S. J., D'AMBRA T. E., HAYCOCK D. A. in J. Pharmacol. Exp. Ther., 264 1352–1363 (1993).

In this test, the $IC_{50}$ of the compounds of formula (I) is less than or equal to 1000 nM.

Their antagonist activity has been shown by means of the model of hypothermia induced by an agonist of the cannabis receptors (CP-55940) in mice, according to the method described by Pertwee R. G. in Marijuana, Harvey D. J. eds, 84 Oxford IRL Press, 263–277 (1985).

In this test, the $ED_{50}$ of the compounds of formula (I) is less than or equal to 50 mg/kg.

The compounds of formula (I) exhibit low toxicity. Their $LD_{50}$ is greater than 40 mg/kg by the subcutaneous route in mice.

The following examples illustrate the invention.

EXAMPLE 1

69.3 mm³ of triethylamine and 110 mg of thien-2-ylsulfonyl chloride are successively added, at room temperature and under an argon atmosphere, to a solution of 61.4 mg of 1-[bis(4-chlorophenyl)methyl]azetidin-3-ylamine in 3 cm³ of dichloromethane. After stirring for 68 hours at room temperature, the reaction mixture is introduced into a Bond Elut® SCX cartridge (3 cm⁵/500 mg), eluting successively with twice 2 cm³ of dichloromethane and then twice 2 cm³ of a 1 M solution of ammonia in methanol. The ammoniacal fractions are pooled and concentrated to dryness under reduced pressure (2.7 kPa). The residue obtained is dissolved in 5 cm³ of dichloromethane, washed with three times 3 cm³ of distilled water, dried over magnesium sulfate, filtered and concentrated to dryness under reduced pressure (2.7 kPa). 60 mg of N-{1-[bis(4-chlorophenyl)methyl]azetidin-3-yl}thien-2-ylsulfonamide are thus obtained in the form of a cream-colored foam [¹H NMR spectrum (300 MHz, CDCl₃, δ in ppm): 2.77 (split t, J=7 and 2 Hz: 2H); 3.40 (split t, J=7 and 2 Hz: 2H); 4.06 (mt: 1H); 4.21 (s: 1H); from 4.85 to 5.25 (broad unresolved complex: 1H); 7.06 (t, J=4.5 Hz: 1H); from 7.15 to 7.35 (mt: 8H); 7.58 (mt: 2H)].

1-[Bis(4-chlorophenyl)methyl]azetidin-3-ylamine may be obtained in the following manner: 400 cm³ of a mixture of methanol and liquid ammonia (50/50 by volume) are added to 27 g of 1-[bis(4-chlorophenyl)methyl]azetidin-3-yl methylsulfonate contained in an autoclave previously cooled to around −60° C. The reaction medium is then stirred at 60° C. for 24 hours and then abandoned in the open air to allow the evaporation of the ammonia and finally concentrated under reduced pressure (2.7 kPa). The residue is taken up in 500 cm³ of a 0.37 N aqueous sodium hydroxide solution and extracted with four times 500 cm³ of ethyl ether. The combined organic phases are washed successively with twice 100 cm³ of distilled water and 100 cm³ of a saturated sodium chloride solution, dried over magnesium sulfate, filtered and concentrated under reduced pressure (2.7 kPa). The residue obtained is purified by flash chromatography on silica gel [eluant: dichloromethane/methanol (95/5 by volume)]. 14.2 g of 1-[bis(4-chlorophenyl)methyl]azetidin-3-ylamine are obtained in the form of an oil which solidifies into a cream-colored solid.

1-[Bis(4-chlorophenyl)methyl]azetidin-3-yl methylsulfonate may be prepared in the following manner: 3.5 cm³ of methylsulfonyl chloride are added, under argon over 10 minutes, to a solution of 12 g of 1-[bis(4-chlorophenyl)methyl]azetidin-3-ol in 200 cm³ of dichloromethane and then the mixture is cooled to +5° C. and 3.8 cm³ of pyridine are poured in over 10 minutes. After stirring for 30 minutes at +5° C. and then for 20 hours at 20° C., the reaction mixture is diluted with 100 cm³ of water and 100 cm³ of dichloromethane. The mixture, which is first filtered, is separated after settling. The organic phase is washed with water and then dried over magnesium sulfate, filtered and concentrated to dryness under reduced pressure (2.7 kPa). The oil obtained is chromatographed on a 40 cm, diameter 3.0 cm), eluting under an argon pressure of 0.5 bar with a mixture of cyclohexane and ethyl acetate (70/30 by volume) and collecting 100-cm³ fractions. Fractions 4 to 15 are combined and concentrated to dryness under reduced pressure (2.7 kPa). 6.8 g of 1-[bis(4-chlorophenyl)methyl]-azetidin-3-yl ester of methylsulfonic acid are obtained in the form of a yellow oil.

1-[Bis(4-chlorophenyl)methyl]azetidin-3-ol may be prepared according to the procedure described by KATRITZKY A. R. et al., J. Heterocycl. Chem., 271 (1994), starting with 35.5 g of [bis(4-chlorophenyl)methyl]-amine hydrochloride and 11.0 cm³ of epichlorohydrin. 9.0 g of 1-[bis(4-chlorophenyl)methyl]azetidin-3-ol are isolated.

[Bis(4-chlorophenyl)methyl]amine hydrochloride may be prepared according to the method described by GRISAR M. et al., J. Med. Chem., 885 (1973).

EXAMPLE 2

By carrying out the operation according to the procedure of Example 1, but starting with 124 mg of 4-methoxyphenylsulfonyl chloride, 12 mg of N-{1-[bis(4-chlorophenyl)methyl]azetidin-3-yl}-4-methoxyphenylsulfonamide are obtained in the form of a cream-colored lacquer [$^1$H NMR spectrum (300 MHz, CDCl$_3$, δ in ppm): 2.70 (split t, J=7 and 2 Hz: 2H) 3.35 (split t, J=7 and 2 Hz: 2H); 3.85 (s: 3H); 3.94 (mt: 1H); 4.18 (s: 1H); 4.83 (d, J=9 Hz: 1H); 6.94 (broad d, J=9 Hz: 2H); 7.22 (s: 8H); 7.75 (broad d, J=9 Hz: 2H)].

EXAMPLE 3

By carrying out the operation according to the procedure of Example 1, but starting with 140 mg of 4-acetamidophenylsulfonyl chloride, 13 mg of N-[4-(N-{1-[bis(4-chlorophenyl)methyl]azetidin-3-yl}sulfamoyl)phenyl]acetamide are obtained in the form of a cream-colored lacquer [$^1$H NMR spectrum (300 MHz, CDCl$_3$, δ in ppm): 2.26 (s: 3H); 2.74 (split t, J=7 and 2 Hz: 2H); 3.39 (split t, J=7 and 2 Hz: 2H); 4.01 (mt: 1H); 4.22 (s: 1H); 4.92 (d, J=9 Hz: 1H); 7.32 (mt: 8H); 7.49 (broad s: 1H); 7.68 (broad d, J=9 Hz: 2H); 7.81 (broad d, J=9 Hz: 2H)].

EXAMPLE 4

By carrying out the operation according to the procedure of Example 1, but starting with 114 mg of 4-methylphenylsulfonyl chloride, 19 mg of N-{1-[bis-(4-chlorophenyl)methyl]azetidin-3-yl}-4-methylphenyl-sulfonamide are obtained in the form of a colorless lacquer [$^1$H NMR spectrum (300 MHz, CDCl$_3$, δ in ppm): 2.42 (s: 3H); 2.71 (split t, J=7 and 2 Hz: 2H); 3.36 (split t, J=7 and 2 Hz: 2H); 3.97 (mt: 1H); 4.19 (s: 1H); 4.81 (d, J=9.5 Hz: 1H); from 7.15 to 7.40 (mt: 10H); 7.71 (broad d, J=8.5 Hz: 2H)].

EXAMPLE 5

By carrying out the operation according to the procedure of Example 1, but starting with 142 mg of 3,4-dimethoxyphenylsulfonyl chloride, 10 mg of N-{1-[bis(4-chlorophenyl)methyl]azetidin-3-yl}-3,4-dimethoxyphenylsulfonamide are obtained in the form of a cream-colored lacquer [$^1$H NMR spectrum (300 MHz, CDCl$_3$, δ in ppm): 2.72 (broad t, J=7.5 Hz: 2H); 3.37 (broad t, J=7.5 Hz: 2H); from 3.85 to 4.00 (mt: 1H); 3.91 (s: 3H); 3.93 (s: 3H); 4.19 (s: 1H); 4.84 (d, J=9 Hz: 1H); 6.90 (d, J=8.5 Hz: 1H); 7.23 (mt: 8H); 7.29 (d, J=2 Hz: 1H); 7.43 (dd, J=8.5 and 2 Hz: 1H)].

EXAMPLE 6

By carrying out the operation according to the procedure of Example 1, but starting with 117 mg of 3-fluorophenylsulfonyl chloride, 13.5 mg of N-{1-[bis(4-chlorophenyl)methyl]azetidin-3-yl}-3-fluorophenyl-sulfonamide are obtained in the form of a cream-colored lacquer [$^1$H NMR spectrum (400 MHz, CDCl$_3$, δ in ppm): 2.79 (split t, J=7 and 2 Hz: 2H); 3.43 (split t, J=7 and 2 Hz: 2H); 4.05 (unresolved complex: 1H); 4.24 (s: 1H); 4.91 (unresolved complex: 1H); from 7.20 to 7.40 (mt: 9H); from 7.50 to 7.65 (mt: 2H); 7.67 (broad d, J=8 Hz: 1H)].

EXAMPLE 7

By carrying out the operation according to the procedure of Example 1, but starting with 147 mg of 3,4-dichlorophenylsulfonyl chloride, 20 mg of N-{1-[bis(4-chlorophenyl)methyl]azetidin-3-yl}-3,4-dichlorophenylsulfonamide are obtained in the form of a cream-colored lacquer [$^1$H NMR spectrum (300 MHz, CDCl$_3$, δ in ppm): 2.77 (split t, J=7 and 2 Hz: 2H); 3.40 (split t, J=7 and 2 Hz: 2H); 3.98 (mt: 1H); 4.21 (s: 1H); from 4.85 to 5.15 (unresolved complex: 1H); from 7.20 to 7.35 (mt: 8H); 7.57 (d, J=8.5 Hz: 1H); 7.65 (dd, J=8.5 and 2 Hz: 1H); 7.93 (d, J=2 Hz: 1H)].

EXAMPLE 8

By carrying out the operation according to the procedure for Example 1, but starting with 121 mg of 3-cyanophenylsulfonyl chloride, 21 mg of N-{1-[bis(4-chlorophenyl)methyl]azetidin-3-yl}-3-cyanophenylsulfonamide are obtained in the form of a cream-colored lacquer [$^1$H NMR spectrum (300 MHz, CDCl$_3$, δ in ppm): 2.76 (split t, J=7 and 2 Hz: 2H); 3.39 (split t, J=7 and 2 Hz: 2H); 3.99 (mt: 1H); 4.21 (s: 1H); from 4.80 to 5.60 (very broad unresolved complex: 1H); from 7.15 to 7.35 (mt: 8H); 7.65 (t, J=8 Hz: 1H); 7.86 (broad d, J=8 Hz: 1H); 8.05 (broad d, J=8 Hz: 1H); 8.13 (broad s: 1H)].

EXAMPLE 9

By carrying out the operation according to the procedure of Example 1, but starting with 142 mg of 2,5-dimethoxyphenylsulfonyl chloride, 31 mg of N-{1-[bis(4-chlorophenyl)methyl]azetidin-3-yl}-2,5-dimethoxyphenylsulfonamide are obtained in the form of a cream-colored lacquer [$^1$H NMR spectrum (300 MHz, CDCl$_3$, δ in ppm): 2.73 (split t, J=7 and 2 Hz: 2H); 3.27 (split t, J=7 and 2 Hz: 2H); 3.80 (s: 3H); from 3.85 to 4.00 (mt: 1H); 3.94 (s: 3H); 4.19 (s: 1H); 5.32 (d, J=8 Hz: 1H); 6.94 (d, J=9 Hz: 1H); 7.05 (dd, J=9 and 3 Hz: 1H); 7.23 (mt: 8H); 7.40 (d, J=3 Hz: 1H)].

EXAMPLE 10

By carrying out the operation according to the procedure of Example 1, but starting with 147 mg of 3-trifluoromethylphenylsulfonyl chloride, 8 mg of N-{1-[bis(4-chlorophenyl)methyl]azetidin-3-yl}-3-trifluoromethylphenylsulfonamide are obtained in the form of a cream-colored lacquer [$^1$H NMR spectrum (300 MHz, CDCl$_3$, δ in ppm): 2.79 (split t, J=7 and 2 Hz: 2H); 3.41 (split t, J=7 and 2 Hz: 2H); 4.03 (mt: 1H); 4.23 (s: 1H); from 4.80 to 5.10 (broad unresolved complex: 1H); from 7.20 to 7.35 (mt: 8H); 7.68 (t, J=8 Hz: 1H); 7.87 (broad d, J=8 Hz: 1H); 8.05 (broad d, J=8 Hz: 1H); 8.15 (broad s: 1H)].

EXAMPLE 11

By carrying out the operation according to the procedure of Example 1, but starting with 136 mg of naphtha-2-ylsulfonyl chloride, 20 mg of N-{1-[bis(4-chlorophenyl)methyl]azetidin-3-yl}naphth-2-yl-sulfonamide are obtained in the form of a cream-colored lacquer [$^1$H NMR spectrum (400 MHz, CDCl$_3$, δ in ppm): 2.74 (mt: 2H); 3.35 (mt: 2H); 4.02 (mt: 1H); 4.17 (s: 1H); 4.96 (unresolved complex: 1H); from 7.10 to 7.30 (mt: 8H); 7.64 (mt: 2H); 7.78 (dd, J=7 and 1.5 Hz: 1H); 7.90 to 8.05 (mt: 3H); 8.41 (broad s: 1H)].

EXAMPLE 12

By carrying out the operation according to the procedure of Example 1, but starting with 136 mg of naphth-1-ylsulfonyl chloride, 52 mg of N-{1-[bis(4-chlorophenyl)methyl]azetidin-3-yl}naphth-1-yl-sulfonamide are obtained in the form of a cream-colored foam [$^1$H NMR spectrum (300 MHz, CDCl$_3$, δ in ppm): 2.63 (split t, J=7 and 2 Hz: 2H); 3.20 (split t, J=7 and 2 Hz: 2H); 3.90 (mt: 1H); 4.12 (s: 1H); 5.26 (unresolved complex: 1H); 7.16 (mt: 8H); 7.52 (t, J=8 Hz: 1H); from 7.55 to 7.75 (mt: 2H); 7.95 (d, J=8.5 Hz: 1H); 8.06 (d, J=8.5 Hz: 1H); 8.23 (dd, J=7.5 and 1 Hz: 1H); 8.64 (d, J=8.5 Hz: 1H)].

EXAMPLE 13

By carrying out the operation according to the procedure of Example 1, but starting with 128 mg of 3,4-difluorophenylsulfonyl chloride, 7 mg of N-{1-[bis(4-chlorophenyl)methyl]azetidin-3-yl}-3,4-difluorophenylsulfonamide are obtained in the form of a cream-colored lacquer [$^1$H NMR spectrum (300 MHz, CDCl$_3$, δ in ppm): 2.76 (broad t, J=7.5 Hz: 2H); 3.39 (broad t, J=7.5 Hz: 2H); 3.98 (mt: 1H); 4.20 (broad s: 1H); from 4.85 to 5.25 (broad unresolved complex: 1H); from 7.15 to 7.35 (mt: 9H); from 7.55 to 7.75 (mt: 2H)].

EXAMPLE 14

By carrying out the operation according to the procedure of Example 1, but starting with 108 mg of 1-methylimidazol-4-ylsulfonyl chloride, 22 mg of N-{1-[bis(4-chlorophenyl)methyl]azetidin-3-yl}-1-methyl-1-H-imidazol-4-ylsulfonamide are obtained in the form of a cream-colored foam [$^1$H NMR spectrum (300 MHz, CDCl$_3$, with addition of a few drops of CD$_3$COOD d4, δ in ppm): 3.22 (mt: 2H); 3.67 (mt: 2H); 3.74 (s: 3H); 4.10 (mt: 1H); 4.65 (broad s: 1H); 7.27 (mt: 8H); 7.47 (broad d, J=1 Hz: 1H); 7.53 (broad d, J=1 Hz: 1H)].

EXAMPLE 15

By carrying out the operation according to the procedure of Example 1, but starting with 152 mg of 4-acetamido-3-chlorophenylsulfonyl chloride, 69 mg of N-[4-(N-{1-[bis(4-chlorophenyl)methyl]azetidin-3-yl}sulfamoyl)-2-chlorophenyl]acetamide are obtained in the form of a cream-colored foam [$^1$H NMR spectrum (300 MHz, CDCl$_3$, δ in ppm): 2.30 (s: 3H); 2.73 (mt: 2H); 3.38 (mt: 2H); 3.97 (mt: 1H); 4.19 (s: 1H); 7.24 (s: 8H); 7.70 (dd, J=7 and 1.5 Hz: 1H); 7.78 (broad s: 1H); 7.86 (d, J=1.5 Hz: 1H); 8.61 (d, J=7 Hz: 1H)].

EXAMPLE 16

0.79 cm$^3$ of triethylamine is added, at room temperature under an argon atmosphere, to a solution of 0.7 g of 1-[bis(4-chlorophenyl)methyl]azetidin-3-ylamine in 25 cm$^3$ of dichloromethane. The mixture is cooled to around 0° C. before adding thereto a solution of 1.2 g of pyrid-3-ylsulfonyl chloride in 25 cm$^3$ of dichloromethane, and then it is stirred at room temperature for 16 hours. The reaction mixture is diluted with 50 cm$^3$ of dichloromethane and is then washed with twice 25 cm$^3$ of distilled water. The organic phase is dried over magnesium sulfate, filtered and concentrated to dryness under reduced pressure (2.7 kPa). The residue obtained is purified by flash chromatography on silica gel [eluant: dichloromethane/methanol (97.5/2.5 by volume)]. 0.7 g of N-{1-[bis(4-chlorophenyl)methyl]azetidin-3-yl}pyrid-3-ylsulfonamide is obtained in the form of a cream-colored foam which solidifies in the presence of isopropanol into a cream-colored powder melting at 164° C.

Pyrid-3-ylsulfonyl chloride may be prepared according to the method described by Breant, P. et al., Synthesis, 10, 822–4 (1983).

EXAMPLE 17

0.214 g of 4-fluorophenylsulfonyl chloride and 0.28 cm$^3$ of triethylamine are added, at room temperature under an argon atmosphere, to a solution of 0.307 g of 1-[bis(4-chlorophenyl)methyl]azetidin-3-ylamine in 10 cm$^3$ of dichloromethane. After stirring for 16 hours at room temperature, the reaction mixture is washed with 10 cm$^3$ of distilled water, dried over magnesium sulfate, filtered and concentrated to dryness under reduced pressure (2.7 kPa). The residue obtained is purified by flash chromatography on silica gel [eluant: dichloromethane/ethyl acetate (100/0 to 95/5 by volume) gradient]. 0.18 g of N-{1-[bis(4-chlorophenyl)methyl]azetidin-3-yl}-4-fluorophenylsulfonamide is obtained in the form of a white foam [$^1$H NMR spectrum (300 MHz, CDCl$_3$, δ in ppm): 2.74 (broad t, J=7.5 Hz: 2H); 2.39 (broad t, J=7.5 Hz: 2H); 3.98 (mt: 1H); 4.20 (s: 1H); 4.79 (d, J=9 Hz: 1H); from 7.10 to 7.35 (mt: 10H); 7.86 (mt: 2H)].

EXAMPLE 18

By carrying out the operation according to the procedure for Example 17, but starting with 0.25 g of quinol-8-ylsulfonyl chloride, 0.36 g of N-{1-[bis(4-chlorophenyl)methyl]azetidin-3-yl}quinol-8-ylsulfonamide is obtained in the form of a white powder [$^1$H NMR spectrum (300 MHz, CDCl$_3$, δ in ppm): 2.63 (split t, J=7 and 2 Hz: 2H); 3.16 (split t, J=7 and 2 Hz: 2H); 3.98 (mt: 1H); 4.11 (s: 1H); 6.77 (d, J=8 Hz: 1H); 7.15 (mt: 8H); 7.61 (dd, J=8 and 4 Hz: 1H); 7.64 (dd, J=8 and 7.5 Hz): 1H); 8.06 (dd, J=8 and 1.5 Hz: 1H); 8.30 (dd, J=8 and 1.5 Hz: 1H); 8.40 (dd, J=7.5 and 1.5 Hz: 1H); 9.09 (dd, J=4 and 1.5 Hz: 1H)].

EXAMPLE 19

By carrying out the operation according to the procedure of Example 17, but starting with 0.14 cm$^3$ of phenylsulfonyl chloride, 0.35 g of N-{1-[bis(4-chlorophenyl)methyl]azetidin-3-yl}phenylsulfonamide is obtained in the form of a white powder [$^1$H NMR spectrum (300 MHz, CDCl$_3$, δ in ppm): 2.75 (broad t, J=7.5 Hz: 2H); 3.40 (broad t, J=7.5 Hz: 2H); 4.03 (mt: 1H); 4.22 (s: 1H); 4.79 (d, J=10 Hz: 1H); 7.31 (s: 8H); from 7.45 to 7.65 (mt: 3H); 7.87 (broad d, J=7.5 Hz: 2H)].

EXAMPLE 20

By carrying out the operation according to the procedure of Example 17, but starting with 0.21 g of (phenylmethyl)sulfonyl chloride, 0.27 g of N-{1-[bis(4-chlorophenyl)methyl]azetidin-3-yl}(phenyl-methyl)sulfonamide is obtained in the form of a white powder [$^1$H NMR spectrum (400 MHz, CDCl$_3$, δ in ppm): 2.76 (split t, J=7 and 2 Hz: 2H); 3.41 (split t, J=7 and 2 Hz: 2H); 3.85 (mt: 1H); 4.20 (s: 1H); 4.23 (s: 2H); 4.46 (d, J=9 Hz: 1H); from 7.25 to 7.45 (mt: 13H)].

EXAMPLE 21

By carrying out the operation according to the procedure of Example 17, but starting with 0.42 g of 3,5-difluorophenylsulfonyl chloride in 30 cm$^3$ of dichloromethane and washing the organic phase with twice 20 cm$^3$ of distilled water. After purification by flash chromatography on silica gel [eluant: dichloromethane/methanol (100/0 to 95/5 by volume) gradient], 0.1 g of N-{1-[bis(4-chlorophenyl)methyl]azetidin-3-yl}-3,5-difluorophenylsulfonamide is obtained in the form of a yellow powder [$^1$H NMR spectrum (300 MHz, CDCl$_3$, δ in ppm): 2.77 (split t, J=7 and 2 Hz: 2H); 3.41 (split t, J=7 and 2 Hz: 2H); 4.01 (mt: 1H); 4.21 (s: 1H); 4.90 (d, J=9 Hz: 1H); 7.02 (tt, J=8.5 and 2.5 Hz: 1H); from 7.20 to 7.35 (mt: 8H); 7.38 (mt: 2H)].

3,5-Difluorophenylsulfonyl chloride may be prepared according to the method described in Patent FR 9615887.

EXAMPLE 22

By carrying out the operation according to the procedure of Example 21, but starting with 0.21 g of pyrid-2-ylsulfonyl chloride and 0.17 cm$^3$ of triethylamine and washing the organic phase with twice 30 cm$^3$ of distilled water. After purification by flash chromatography on silica gel [eluant: dichloromethane/methanol (100/0 to 98/2 by volume) gradient], 0.3 g of N-{1-[bis(4-chlorophenyl)methyl]azetidin-3-yl}pyrid-2-sulfonamide is obtained in the form of a white powder [$^1$H NMR spectrum (300 MHz, CDCl$_3$, δ in ppm): 2.78 (split t, J=7 and 2 Hz: 2H); 3.35 (split t, J=7 and 2 Hz: 2H); 4.12 (mt: 1H); 4.20 (s: 1H); 5.30 (d, J=9 Hz: 1H); from 7.15 to 7.35 (mt: 8H); 7.47 (ddd, J=7.5 and 5 and 1 Hz: 1H); 7.90 (split t, J=7.5 and 2 Hz: 1H); 7.98 (broad d, J=7.5 Hz: 1H); 8.65 (broad d, J=5 Hz: 1H)].

Pyrid-2-ylsulfonyl chloride may be prepared according to the method described by Corey, E. J. et al., J. Org. Chem. (1989), 54(2), 389–93.

EXAMPLE 23

0.104 cm$^3$ of pyrrolidine is added, at room temperature, to 0.24 g of N-{-[bis(4-chlorophenyl)-methyl]azetidin-3-yl}-(3,5-difluorophenyl)sulfonamide in solution in 6 cm$^3$ of dimethyl sulfoxide and then the mixture is heated for 18 hours at 90° C. The reaction mixture is diluted with 30 cm$^3$ of dichloromethane and washed with three times 30 cm$^3$ of distilled water. The organic phased is dried over magnesium sulfate, filtered and concentrated to dryness under reduced pressure (2.7 kPa). The residue is purified by flash chromatography on silica gel, eluting with dichloromethane. 50 mg of N-{1-[bis(4-chlorophenyl)methyl]azetidin-3-yl}-(3-fluoro-5-pyrrolidin-1-ylphenyl)sulfonamide are thus obtained in the form of a white powder [$^1$H NMR spectrum (600 MHz, CDCl$_3$ with addition of a few drops of CD$_3$COOD d4, δ in ppm): 2.04 (mt: 4H); from 3.20 to 3.35 (mt: 6H); 3.60 (t, J=8.5 Hz: 2H); 4.14 (mt: 1H); 4.57 (s: 1H); 6.31 (broad d, J=11.5 Hz: 1H); 6.70 (broad d, J=8.5 Hz: 1H); 6.72 (broad s: 1H); from 7.20 to 7.35 (mt: 8H)].

EXAMPLE 24

A solution of 0.26 g of N-{1-[bis(4-chlorophenyl)methyl]azetidin-3-yl}-4-fluorophenylsulfonamide in 5 cm$^3$ of tetrahydrofuran is added, at room temperature under an argon atmosphere, to a suspension of 20.5 mg of 80% sodium hydride in 10 cm$^3$ of tetrahydrofuran. After stirring for 1 hour at around 20° C., 60 mm$^3$ of iodomethane are added and then after stirring for an additional 16 hours, the suspension is supplemented with 30 cm$^3$ of ethyl acetate and 20 cm$^3$ of distilled water. The organic phase is dried over magnesium sulfate, filtered and concentrated to dryness under reduced pressure (2.7 kPa). The residue is purified by flash chromatography on silica gel [eluant: cyclohexane/ethyl acetate (90/10 by volume)]. 19 mg of N-{1-[bis(4-chlorophenyl)methyl]azetidin-3-yl}-N-methyl-4-fluorophenylsulfonamide are thus obtained in the form of a white powder [$^1$H NMR spectrum (300 MHz, CDCl$_3$, δ in ppm): 2.69 (s: 3H); 3.02 (split t, J=7 and 2 Hz: 2H); 3.35 (split t, J=7 and 2 Hz: 2H); 3.91 (mt: 1H); 4.27 (s: 1H); from 7.15 to 7.35 (mt: 10H); 7.75 (dd, J=9 and 5 Hz: 2H)].

EXAMPLE 25

By carrying out the operation according to the procedure of Example 24, but starting with 0.25 g of N-{1-[bis(4-chlorophenyl)methyl]azetidin-3-yl}-quinol-8-ylsulfonamide and 18 mg of 80% sodium hydride. After purification by flash chromatography on silica gel [eluant: cyclohexane/ethyl acetate (80/20 by volume)], 70 mg of N-{1-[bis(4-chlorophenyl)methyl]azetidin-3-yl}-N-methylquinol-8-ylsulfonamide are obtained [$^1$H NMR spectrum (300 MHz, CDCl$_3$, δ in ppm): from 3.00 to 3.10 (mt: 2H); 3.05 (s: 3H); 3.35 (mt: 2H); 4.27 (s: 1H); 4.93 (mt: 1H); from 7.15 to 7.35 (mt: 8H); 7.50 (dd, J=8.5 and 4 Hz: 1H); 7.62 (dd, J=8 and 8.5 Hz: 1H); 8.03 (dd, J=8.5 and 1.5 Hz:

1H); 8.22 (dd, J=8.5 and 1.5 Hz: 1H); 8.48 (dd, J=8 and 1.5 Hz: 1H); 8.98 (dd, J=4 and 1.5 Hz: 1H)].

EXAMPLE 26

By carrying out the operation according to the procedure of Example 24, but starting with 0.21 g of N-{1-[bis(4-chlorophenyl)methyl]azetidin-3-yl}-phenylsulfonamide, 17 mg of 80% sodium hydride and introducing iodomethane in two portions at an interval of 3 hours. 80 mg of N-{1-[bis(4-chlorophenyl)methyl]azetidin-3-yl}-N-methylphenylsulfonamide are thus obtained in the form of a white lacquer [$^1$H NMR spectrum (300 MHz, CDCl$_3$, δ in ppm): 2.70 (s: 3H); 3.03 (broad t, J=7.5 Hz: 2H); 3.37 (broad t, J=7.5 Hz: 2H); 3.94 (mt: 1H); 4.28 (s: 1H); from 7.20 to 7.35 (mt: 8H); from 7.45 to 7.65 (mt: 3H); 7.74 (broad d, J=8 Hz: 2H)].

EXAMPLE 27

By carrying out the operation according to the procedure of Example 26, but starting with 0.17 9 of N-{1-[bis(4-chlorophenyl)methyl]azetidin-3-yl}-(phenylmethyl)sulfonamide, 14 mg of 80% sodium hydride and maintaining stirred for 48 hours at 20° C. After purification by flash chromatography on silica gel [eluant: dichloromethane/ethyl acetate (95/5 by volume)], 120 mg of N-{1-[bis(4-chlorophenyl)methyl]azetidin-3-yl}-N-methyl(phenylmethyl)sulfonamide are obtained in the form of a white foam [$^1$H NMR spectrum (300 MHz, CDCl$_3$, δ in ppm): 2.81 (s: 3H); 2.88 (split t, J=7 and 2 Hz: 2H); 3.16 (split t, J=7 and 2 Hz: 2H); from 4.10 to 4.25 (mt: 4H); from 7.20 to 7.40 (mt: 13H)].

EXAMPLE 28

A solution of 0.307 g of 1-[bis(4-chlorophenyl)methyl]azetidin-3-ylamine is added dropwise, at room temperature, to a solution of 0.412 g of 1,3-benzenedisulfonic acid dichloride and 0.165 cm$^3$ of triethylamine in 10 cm$^3$ of acetonitrile. After stirring for 3 hours at room temperature, 0.28 cm$^3$ of a 20% solution of ammonia is added and the reaction mixture is left at room temperature. After 18 hours, the mixture is filtered and concentrated to dryness under reduced pressure (2.7 kPa). After chromatography on a silica gel column (particle size 0.06–0.200 mm, height 35 cm, diameter 2 cm), eluting under an argon pressure of 0.9 bar with dichloromethane and then a mixture of dichloromethane+1% methanol and then a mixture of dichloromethane+2% methanol by volume and collecting 30-cm$^3$ fractions, fractions 23 to 34 are combined and concentrated to dryness under reduced pressure (2.7 kPa) to give 90 mg of N-{1-[bis(4-chlorophenyl)methyl]azetidin-3-yl}-3-sulfamoylphenylsulfonamide in the form of a white solid [$^1$H NMR spectrum (300 MHz, CDCl$_3$, δ in ppm): 2.78 (broad t, J=7 Hz: 2H); 3.35 (broad t, J=7 Hz: 2H); 4.01 (mt: 1H); 4.24 (s: 1H); 5.27 (unresolved complex: 2H); 5.61 (unresolved complex: 1H); from 7.15 to 7.35 (mt: 8H); 7.67 (t, J=8 Hz: 1H); 8.04 (broad d, J=8 Hz: 1H); 8.12 (broad d, J=8 Hz: 1H); 8.49 (broad s: 1H)].

EXAMPLE 29

0.031 cm$^3$ of diisopropylcarbodiimide, a solution of 30 mg of 1-[bis(4-chlorophenyl)methyl]azetidin-3-ylamine in 0.5 cm$^3$ of anhydrous dichloromethane, and 3 cm$^3$ of anhydrous dichloromethane are added to a solution of 80.1 mg of benzenesulfonylacetic acid, 27 mg of hydroxybenzotriazole in solution in 0.5 cm$^3$ of dimethylformamide under an inert argon atmosphere, at a temperature in the region of 23° C. After 17 hours at a temperature in the region of 23° C., the reaction mixture is loaded onto a 3-cm$^3$ SPE cartridge containing 1 g of SCX phase preconditioned with methanol. After washing with twice 5 cm$^3$ of methanol and then 4 cm$^3$ of 0.1 N ammoniacal methanol, the expected product is eluted with 4 cm$^3$ of 1 N ammoniacal methanol. The fraction containing the expected product is evaporated under an air stream at a temperature in the region of 45° C. and then dried under reduced pressure (1 mbar) at a temperature in the region of 40° C. 2-Benzenesulfonyl-N-{1-[bis(4-chlorophenyl)methyl]azetidin-3-yl}acetamide is thus obtained in the form of a white solid [$^1$H NMR spectrum (500 MHz, CDCl$_3$, δ in ppm): 2.96 (mt: 2H) 3.51 (mt: 2H); 4.00 (s: 2H); 4.34 (unresolved complex: 1H); 4.48 (mt: 1H); 7.10 (unresolved complex: 1H); from 7.20 to 7.45 (mt: 8H); 7.57 (t, J=8 Hz: 2H); 7.70 (t, J=8 Hz: 1H); 7.90 (d, J=8 Hz: 2H)].

EXAMPLE 30

0.031 cm$^3$ of diisopropylcarbodiimide, a solution of 30 mg of 1-[bis(4-chlorophenyl)methyl]azetidin-3-ylamine in 0.5 cm$^3$ of anhydrous dichloromethane, and 3 cm$^3$ of anhydrous dichloromethane are added to a solution of 85.7 mg of toluenesulfonylacetic acid, 27 mg of hydroxybenzotriazole in solution in 0.5 cm$^3$ of dimethylformamide under an inert argon atmosphere, at a temperature in the region of 23° C. After 17 hours at a temperature in the region of 23° C., the reaction mixture is loaded onto a 3-cm$^3$ SPE cartridge containing 1 g of SCX phase preconditioned with methanol. After washing with twice 5 cm$^3$ of methanol and then 4 cm$^3$ of 0.1 N ammoniacal methanol, the expected product is eluted with 4 cm$^3$ of 1 N ammoniacal methanol. The fraction containing the expected product is evaporated under an air stream at a temperature in the region of 45° C. and then dried under reduced pressure (1 mbar) at a temperature in the region of 40° C. N-{1-[bis(4-chlorophenyl)methyl]-azetidin-3-yl}-2-(toluene-4-sulfonyl)acetamide is obtained in the form of a yellow lacquer [$^1$H NMR spectrum (500 MHz, CDCl$_3$, δ in ppm) 2.85 (t, J=7 Hz: 2H); 3.07 (s: 3H); 3.48 (t, J=7 Hz: 2H); 4.24 (s: 1H); 4.49 (mt: 1H); 7.19 (broad d, J=6 Hz: 1H); from 7.20 to 7.40 (mt: 8H); 8.40 (s: 1H)].

EXAMPLE 31

By carrying out the operation according to the procedure of Example 30, starting with 85.7 mg of 3-chloro-4-methylsulfonylthiophene-2-carboxylic acid, 27 mg of hydroxybenzotriazole in solution in 0.5 cm$^3$ of dimethylformamide, 0.031 cm$^3$ of diisopropylcarbodiimide, a solution of 30 mg of 1-[bis(4-chlorophenyl)methyl]azetidin-3-ylamine in 0.5 cm$^3$ of anhydrous dichloromethane, and 3 cm$^3$ of anhydrous dichloromethane, (3-chloro-4-methylsulfonylthiophene-2-carboxy)-{1-[bis(4-chlorophenyl)methyl]azetidin-3-yl}amide is obtained in the form of a yellow lacquer [$^1$H NMR spectrum (500 MHz, CDCl$_3$, δ in ppm): 2.44 (s: 3H) ; 2.96 (unresolved complex: 2H); 3.52 (unresolved complex: 2H); 3.98 (s: 2H); 4.35 (unresolved complex: 1H); 4.49 (mt: 1H); from 7.00 to 7.30 (broad unresolved complex: 1H); from 7.20 to 7.45 (mt: 10H); 7.76 (d, J=8 Hz: 2H)].

EXAMPLE 32

By carrying out the operation according to the procedure of Example 30, starting with 96.1 mg of 3-(2-phenylethylenesulfonyl)propionic acid, 27 mg of hydroxybenzotriazole in solution in 0.5 cm$^3$ of dimethylformamide, 0.031 cm³ of diisopropylcarbodiimide, a solution of 30 mg of 1-[bis(4-chlorophenyl)methyl]azetidin-3-ylamine in 0.5 cm³ of anhydrous dichloromethane, and 3 cm³ of anhydrous dichloromethane, N-{1-[bis(4-chlorophenyl)methyl]azetidin-3-yl}-3-(2-phenylethylenesulfonyl)propionamide is obtained in the form of a white foam [¹H NMR spectrum (500 MHz, CDCl₃, δ in ppm): 2.64 (t, J=7 Hz: 2H); 2.88 (unresolved complex: 2H); 3.33 (t, J=7 Hz: 2H); 3.49 (unresolved complex: 2H); 4.29 (unresolved complex: 1H); 4.48 (mt: 1H); from 5.90 to 6.15 (broad unresolved complex: 1H); 6.41 (d, J=12 Hz: 1H); 7.17 (d, J=12 Hz: 1H); from 7.20 to 7.35 (mt: 8H); 7.41 (mt: 3H); 7.64 (mt: 2H)].

EXAMPLE 33

By carrying out the operation according to the procedure of Example 31, starting with 58.5 mg of 4-methylsulfonylbenzoic acid, 26.4 mg of hydroxybenzotriazole in solution in 0.5 cm³ of dimethylformamide, 0.0302 cm³ of diisopropylcarbodiimide, a solution of 30 mg of 1-[bis(4-chlorophenyl)methyl]azetidin-3-ylamine in 0.5 cm³ of anhydrous dichloromethane, and 3 cm³ of anhydrous dichloromethane, N-{1-[bis(4-chlorophenyl)methyl]azetidin-3-yl}-4-methylsulfonylbenzamide is obtained in the form of a white crystals [¹H NMR spectrum (300 MHz, CDCl₃, δ in ppm): 3.03 (mt: 2H) 3.09 (s: 3H); 3.61 (broad t, J=7.5 Hz: 2H); 4.35 (s: 1H); 4.73 (mt: 1H); 6.55 (broad d, J=7.5 Hz: 1H); from 7.20 to 7.35 (mt: 8H); 7.96 (d, J=8 Hz: 2H); 8.03 (d, J=8 Hz: 2H)].

EXAMPLE 34

By carrying out the operation according to the procedure of Example 31, starting with 58.5 mg of 3-phenylsulfonylpropionic acid, 26.4 mg of hydroxybenzotriazole in solution in 0.5 cm³ of dimethylformamide, 0.0302 cm³ of diisopropylcarbodiimide, a solution of 30 mg of 1-[bis(4-chlorophenyl)methyl]azetidin-3-ylamine in 0.5 cm³ of anhydrous dichloromethane, and 3 cm³ of anhydrous dichloromethane, N-{1-[bis(4-chlorophenyl)methyl]azetidin-3-yl}-4-methanesulfonylbenzamide is obtained in the form of a lacquer [¹H NMR spectrum (300 MHz, CDCl₃, δ in ppm): 2.71 (t, J=7.5 Hz: 2H) 2.86 (mt: 2H); from 3.40 to 3.55 (mt: 4H); 4.26 (s: 1H); 4.45 (mt: 1H); 6.22 (broad d, J=7.5 Hz: 1H); from 7.20 to 7.35 (mt: 8H); 7.59 (broad t, J=7.5 Hz: 2H); 7.69 (tt, J=7.5 and 1.5 Hz: 1H); 7.93 (broad d, J=7.5 Hz: 2H)].

EXAMPLE 35

By carrying out the operation according to the procedure of Example 31, starting with 60.2 mg of 5-methylsulfonylthiophene-2-carboxylic acid, 26.4 mg of hydroxybenzotriazole in solution in 0.5 cm³ of dimethylformamide, 0.0302 cm³ of diisopropylcarbodiimide, a solution of 30 mg of 1-[bis(4-chlorophenyl)methyl]azetidin-3-ylamine in 0.5 cm³ of anhydrous dichloromethane, and 3 cm³ of anhydrous dichloromethane, (5-methylsulfonylthiophene-2-carboxy)-{1-[bis(4-chlorophenyl)methyl]azetidin-3-yl}amide is obtained in the form of white crystals [¹H NMR spectrum (300 MHz, CDCl₃, δ in ppm): 3.03 (mt: 2H); 3.21 (s: 3H); 3.57 (dd, J=8 and 7.5 Hz: 2H); 4.34 (s: 1H); 4.67 (mt: 1H); 6.40 (broad d, J=7.5 Hz: 1H); from 7.20 to 7.35 (mt: 8H); 7.48 (d, J=4 Hz: 1H); 7.67 (d, J=4 Hz: 1H)].

EXAMPLE 36

By carrying out the operation according to the procedure of Example 31, starting with 71.9 mg of 5-methylsulfonyl-3-methyl-4-vinylthiophene-2-carboxylic acid, 26.4 mg of hydroxybenzotriazole in solution in 0.5 cm³ of dimethylformamide, 0.0302 cm³ of diisopropylcarbodiimide, a solution of 30 mg of 1-[bis(4-chlorophenyl)methyl]azetidin-3-ylamine in 0.5 cm³ of anhydrous dichloromethane, and 3 cm³ of anhydrous dichloromethane, (5-methylsulfonyl-3-methyl-4-vinylthiophene-2-carboxy){1-[bis-(4-chlorophenyl)methyl]azetidin-3-yl}amide is obtained in the form of a white powder [¹H NMR spectrum (300 MHz, CDCl₃, δ in ppm): 2.47 (s: 3H); 2.97 (mt: 2H); 3.14 (s: 3H); 3.57 (dd, J=8 and 7.5 Hz: 2H); 4.32 (s: 1H); 4.65 (mt: 1H); 5.69 (dd, J=18 and 1 Hz: 1H); 5.77 (dd, J=12 and 1 Hz: 1H); 6.30 (broad d, J=7.5 Hz: 1H); 6.96 (dd, J=18 and 12 Hz: 1H); from 7.20 to 7.35 (mt: 8H)].

EXAMPLE 37

By carrying out the operation according to the procedure of Example 31, starting with 62.6 mg of 3-methylsulfonylmethylbenzoic acid, 26.4 mg of hydroxybenzotriazole in solution in 0.5 cm³ of dimethylformamide, 0.0302 cm³ of diisopropylcarbodiimide, a solution of 30 mg of 1-[bis(4-chlorophenyl)methyl]azetidin-3-ylamine in 0.5 cm³ of anhydrous dichloromethane, and 3 cm³ of anhydrous dichloromethane, (5-methylsulfonyl-3-methyl-4-vinylthiophene-2-carboxy){1-[bis(4-chlorophenyl)methyl]azetidin-3-yl}amide is obtained in the form of white needles [¹H NMR spectrum (300 MHz, (CD₃)₂SO d6 with addition of CDCl₃, δ in ppm): 2.84 (s: 3H) ; 3.02 (broad t, J=7 Hz: 2H); 3.48 (t, J=7 Hz: 2H); 4.38 (s: 3H); 4.53 (mt: 1H); 7.21 (d, J=8 Hz: 4H); 7.34 (d, J=8 Hz: 4H); 7.40 (t, J=7.5 Hz: 1H); 7.53 (broad d, J=7.5 Hz: 1H); 7.84 (broad d, J=7.5 Hz: 1H); 7.89 (broad s: 1H); 8.54 (d, J=7 Hz: 1H)].

EXAMPLE 38

(RS)-N-{1-[(4-Chlorophenyl)pyridin-3-ylmethyl]azetidin-3-yl}-3,5-difluorobenzenesulfonamide may be obtained in the following manner: 0.46 g of potassium carbonate and 41 mg of potassium iodide are added to a mixture of 0.3 g of (RS)-3-[bromo-(4-chlorophenyl)methyl]pyridine hydrobromide and 0.28 g of N-azetidin-3-yl-3,5-difluorobenzenesulfonamide hydrochloride in 20 cm³ of acetonitrile and then the mixture is heated under reflux for 4 hours. After cooling to a temperature in the region of 20° C., the insoluble matter is removed by filtration and then concentrated to dryness under reduced pressure. The residue obtained is taken up in 100 cm³ of ethyl acetate. The organic phase is washed with twice 50 cm³ of water, dried over magnesium sulfate in the presence of animal charcoal, filtered on Celite and then concentrated to dryness under reduced pressure. 230 mg of an orange-colored solid are obtained, which solid is dissolved in a cyclohexane-ethyl acetate mixture (50-50 mixture by volume) and purified by chromatography under pressure on a cartridge of 10 g of silica with the same eluting mixture, with a flow rate of 6 cm³/minute. Fractions 22 to 56 are combined and concentrated to dryness under reduced pressure. 100 mg of (RS)-N-{1-[(4-chlorophenyl)pyridin-3-ylmethyl]azetidin-3-yl}-3,5-difluorobenzenesulfonamide are thus obtained in the form of a pale yellow foam melting at 70° C. [¹H NMR spectrum (300 MHz, CDCl₃, δ in ppm): 2.81 (mt: 2H); 3.42 (mt: 2H); 4.03 (mt: 1H); 4.29 (s: 1H); 5.43 (d, J=9 Hz: 1H); 7.01 (tt, J=9 and 2.5 Hz: 1H); 7.22 (dd, J=8 and 5 Hz: 1H); 7.28 (mt: 4H) ; 7.36 (mt: 2H); 7.62 (broad d, J=8 Hz: 1H); 8.48 (dd, J=5 and 1 Hz: 1H); 8.59 (d, J=1 Hz: 1H)].

(RS)-3-[Bromo-(4-chlorophenyl)methyl]pyridine is obtained in the following manner: 3.5 cm³ of a 48% solution of hydrobromic acid in acetic acid and 1 cm³ of acetyl bromide are added to 1.5 g of (4-chlorophenyl)pyridin-3-ylmethanol. The amber-colored mixture thus obtained is heated under reflux for 4 hours and then cooled to 20° C., concentrated to dryness at 40° C. under 2.7 kPa, leading to 1.53 g of (RS)-3-[bromo-(4-chlorophenyl)methyl]pyridine (Rf=75/90, 254 nm, silica plates, reference 1.05719, Merck KGaA, 64271 Darmstadt, Germany).

N-Azetidin-3-yl-3,5-difluorobenzenesulfonamide hydrochloride may be prepared in the following manner: in a 2000-cm³ hydrogenator, a solution of 7.5 g of N-(1-benzhydrylazetidin-3-yl)-3,5-difluorobenzenesulfonamide in a mixture of 10 cm³ of concentrated hydrochloric acid (36% by weight), 1.7 cm³ of acetic acid and 500 cm³ of methanol is hydrogenated in the presence of 4.21 g of palladium hydroxide on carbon (20% by weight of catalyst) under 1.7 bar of hydrogen for about 20 hours. The catalyst is removed by filtration on a bed of celite and then the filtrate is concentrated to dryness under reduced pressure. The residue obtained is beaten with 100 cm³ of diisopropyl ether for about 16 hours at a temperature in the region of 20° C. The suspension is filtered and the solid residue is again beaten with 100 cm³ of diethyl ether at a temperature in the region of 20° C. After filtration, the paste obtained is dried under reduced pressure at a temperature in the region of 40° C. 5.52 g of N-azetidin-3-yl-3,5-difluorobenzenesulfonamide hydrochloride are thus obtained in the form of a white powder.

N-(1-Benzhydrylazetidin-3-yl)-3,5-difluorobenzenesulfonamide may be prepared in the following manner: 5.1 g of 3,5-difluorobenzenesulfonyl chloride and then 4.2 cm³ of triethylamine are successively added to a suspension of 5 g of 1-benzhydrylazetidin-3-ylamine in 80 cm³ of dichloromethane at a temperature in the region of 20° C. After stirring for 20 hours at a temperature in the region of 20° C., 50 cm³ of water are added. The decanted organic phase is washed with twice 50 cm³ of water, dried over magnesium sulfate and concentrated to dryness under reduced pressure. 8.99 g of a yellow oil are thus obtained, which oil crystallizes little by little. 4.5 g of this product is purified by chromatography under pressure on 500 g of Amicon silica (diameter of the particles from 0.020 to 0.045 mm), eluting with a methanol-dichloromethane (1–99 by volume) mixture. The fractions containing the desired product are combined and concentrated to dryness under reduced pressure to give 3.58 g of N-(1-benzhydrylazetidin-3-yl)-3,5-difluorobenzenesulfonamide in the form of a beige powder. The remaining quantity of the preceding yellow oil is purified under the same conditions and provides 3.92 g of N-(1-benzhydrylazetidin-3-yl)-3,5-difluorobenzenesulfonamide in the form of a beige powder.

1-Benzhydrylazetidin-3-ylamine may be prepared as described in J. Antibiot., 39(9), 1243–1256, 1986.

3,5-Difluorobenzenesulfonyl chloride may be prepared as described in Patent: FR 2757509.

EXAMPLE 39

(RS)-N-{1-[(4-Chlorophenyl)pyrimidin-5-ylmethyl]azetidin-3-yl}-3,5-difluorobenzenesulfonamide may be obtained by carrying out the procedure as for the preparation of (RS)-N-{1-[(4-chlorophenyl)pyridin-3-ylmethyl]azetidin-3-yl}-3,5-difluorobenzenesulfonamide: starting with 0.64 g of (RS)-5-[bromo-(4-chlorophenyl)methyl]-pyrimidine hydrobromide, 0.5 g of N-azetidin-3-yl-3,5-difluorobenzenesulfonamide hydrochloride in 20 cm³ of acetonitrile, 1.213 g of potassium carbonate and 379 mg of potassium iodide, 71 mg of (RS)-N-{1-[(4-chlorophenyl)pyrimidin-5-ylmethyl]-azetidin-3-yl}-3,5-difluorobenzenesulfonamide are thus obtained in the form of a yellow foam [$^1$H NMR spectrum (300 MHz, CDCl$_3$, δ in ppm) 2.83 (mt: 2H); 3.46 (mt: 2H); 4.03 (mt: 1H); 4.30 (s: 1H); 5.00 (d, J=9 Hz: 1H); 7.04 (tt, J=9 and 2.5 Hz: 1H); from 7.20 to 7.35 (mt: 4H).; 7.37 (mt: 2H); 8.69 (s: 2H); 9.09 (s: 1H)].

(RS)-5-[Bromo-(4-chlorophenyl)-methyl]-pyrimidine may be obtained by carrying out the procedure as for the preparation of (RS)-3-[bromo-(4-chlorophenyl)methyl]pyridine using (4-chlorophenyl)pyrimidin-5-ylmethanol as raw material.

(4-Chlorophenyl)pyrimidin-5-ylmethanol may be prepared by carrying out the procedure as for (4-chlorophenyl)pyridin-3-ylmethanol, starting with pyrimidine-5-carboxaldehyde and 4-chlorophenylmagnesium bromide.

The medicaments according to the invention consist of a compound of formula (I) or an isomer or a salt of such a compound, in the pure state or in the form of a composition in which it is combined with any other pharmaceutically compatible product which may be inert or physiologically active. The medicaments according to the invention may be used orally, parenterally, rectally or topically.

As solid compositions for oral administration, tablets, pills, powders (gelatin capsules, sachets) or granules may be used. In these compositions, the active ingredient according to the invention is mixed with one or more inert diluents, such as starch, cellulose, sucrose, lactose or silica, under an argon stream. These compositions may also comprise substances other than diluents, for example one or more lubricants such as magnesium stearate or talc, a coloring, a coating (sugar-coated tablets) or a glaze.

As liquid compositions for oral administration, there may be used pharmaceutically acceptable solutions, suspensions, emulsions, syrups and elixirs containing inert diluents such as water, ethanol, glycerol, vegetable oils or paraffin oil. These compositions may comprise substances other than diluents, for example wetting, sweetening, thickening, flavoring or stabilizing products.

Sterile compositions for parenteral administration may be preferably solutions which are aqueous or nonaqueous, suspensions or emulsions. As solvent or vehicle, there may be used water, propylene glycol, polyethylene glycol, vegetable oils, in particular olive oil, injectable organic esters, for example ethyl oleate or other suitable organic solvents. These compositions may also contain adjuvants, in particular wetting, isotonizing, emulsifying, dispersing and stabilizing agents. Sterilization may be carried out in several ways, for example by asepticizing filtration, by incorporating sterilizing agents into the composition, by irradiation or by heating. They may also be prepared in the form of sterile solid compositions which may be dissolved at the time of use in sterile water or any other injectable sterile medium.

Compositions for rectal administration are suppositories or rectal capsules which contain, in addition to the active product, excipients such as cocoa butter, semisynthetic glycerides or polyethylene glycols.

Compositions for topical administration may be, for example, creams, lotions, collyria, collutoria, nasal drops or aerosols.

In human therapy, the compounds according to the invention are particularly useful for the treatment and/or prevention of psychoses including schizophrenia, anxiety disorders, depression, epilepsy, neurodegeneration, cerebellar and spinocerebellar disorders, cognitive disorders, cranial trauma, panic attacks, peripheral neuropathies, glaucomas, migraine, Parkinson's disease, Alzheimer's disease, Huntington's chorea, Raynaud's syndrome, tremor, obsessive-compulsive disorder, senile dementia, thymic disorders, Tourette's syndrome, tardive dyskinesia, bipolar disorders, cancers, movement disorders induced by medicaments, dystonia, endotoxemic shocks, hemorrhagic shocks, hypotension, insomnia, immunological diseases, multiple sclerosis, vomiting, asthma, appetite disorders (bulimia, anorexia), obesity, memory disorders, intestinal transit disorders, in weaning from chronic treatments and alcohol or drug abuse (opioids, barbiturates, cannabis, cocaine, amphetamine, phencyclide, hallucinogens, benzodiazepines for example), as analgesics or potentiators of the analgesic activity of the narcotic and nonnarcotic drugs.

The doses depend on the desired effect, the duration of the treatment and the route of administration used; they are generally between 5 mg and 1000 mg per day orally for an adult with unit doses ranging from 1 mg to 250 mg of active substance.

In general, the doctor will determine the appropriate dosage depending on the age, weight and any other factors specific to the subject to be treated.

The following examples illustrate the compositions according to the invention:

Example A

Gelatin capsules containing a dose of 50 mg of active product and having the following composition are prepared according to the usual technique:

| | |
|---|---|
| Compound of formula (I) | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg. |

Example B

Tablets containing a dose of 50 mg of active product and having the following composition are prepared according to the usual technique:

| | |
|---|---|
| Compound of formula (I) | 50 mg |
| Lactose | 104 mg |
| Cellulose | 40 mg |
| Polyvidone | 10 mg |
| Sodium carboxymethylstarch | 22 mg |
| Talc | 10 mg |
| Magnesium stearate | 2 mg |
| Colloidal silica | 2 mg |
| Mixture of hydroxymethylcellulose, glycerin, titanium oxide (72-3.5-24.5) qs 1 finished film-coated tablet containing. | 245 mg |

Example C

An injectable solution containing 10 mg of active product and having the following composition is prepared:

| | |
|---|---|
| Compound of formula (I) | 10 mg |
| Benzoic acid | 80 mg |
| Benzyl alcohol | 0.06 ml |
| Sodium benzoate | 80 mg |
| Ethanol, 95% | 0.4 ml |
| Sodium hydroxide | 24 mg |
| Propylene glycol | 1.6 ml |
| Water | qs 4 ml. |

What is claimed is:
1. A compound of formula:

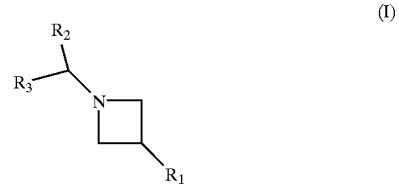

in which
$R_1$ represents a radical —NHCOR$_4$ or —N(R$_5$)—Y—R$_6$;
Y is CO or SO$_2$;
$R_2$ and $R_3$, which are identical or different, represent either an aromatic radical selected from phenyl, naphthyl and indenyl, these aromatics being unsubstituted or substituted with one or more halogen atoms or alkyl, alkoxy, formyl, hydroxyl, trifluoromethyl, trifluoromethoxy, —CO-alk, cyano, —COOH, —COOalk, —CONR$_7$R$_8$, —CO—NH—NR$_9$R$_{10}$, alkylsulfanyl, alkylsulfinyl, alkyl-sulfonyl, alkylsulfanylalkyl, alkylsulfinylalkyl, alkylsulfonylalkyl, hydroxyalkyl or -alk-NR$_7$R$_8$ radicals; or a heteroaromatic radical selected from benzofuryl, benzothiazolyl, benzothienyl, benzoxazolyl, chromanyl, 2,3-dihydrobenzofuryl, 2,3-dihydrobenzothienyl, pyrimidinyl, furyl, imidazolyl, isochromanyl, isoquinolyl, pyrrolyl, pyridyl, quinolyl, 1,2,3,4-tetrahydro-isoquinolyl, thiazolyl and thienyl rings, it being possible for these heteroaromatic radicals to be unsubstituted or substituted with a halogen atom or an alkyl, alkoxy, hydroxyl, trifluoromethyl, trifluoromethoxy, cyano, —COOH, —COOalk, —CO—NH—NR$_9$R$_{10}$, —CONR$_7$R$_8$, -alk-NR$_9$R$_{10}$, alkylsulfanyl, alkylsulfinyl, alkylsulfonyl, alkylsulfanylalkyl, alkylsulfinylalkyl, alkylsulfonylalkyl or hydroxyalkyl radical;
$R_4$ represents a radical -alk-SO$_2$—R$_{11}$, -alk-SO$_2$—CH═CH—R$_{11}$, Het substituted with —SO$_2$—R$_{11}$ or phenyl substituted with —SO$_2$—R$_{11}$ or -alk-SO$_2$—R$_{11}$;
$R_5$ represents a hydrogen atom or an alkyl radical;
$R_6$ represents a phenylalkyl, Het or Ar radical;
$R_7$ and $R_8$, which are identical or different, represent a hydrogen atom or an alkyl radical or alternatively $R_7$ and $R_8$ together with the nitrogen atom to which they are attached form a 3- to 10-membered saturated mono- or bicyclic heterocycle, optionally further having another heteroatom selected from oxygen, sulfur and nitrogen and being optionally substituted with one or more alkyl radicals,
$R_9$ and $R_{10}$, which are identical or different, represent a hydrogen atom or an alkyl, —COOalk, cycloalkyl, alkylcycloalkyl, -alk-O-alk or hydroxyalkyl radical or alternatively $R_9$ and $R_{10}$ together with the nitrogen atom to which they are attached form a 3- to 10-membered saturated or unsaturated mono- or bicyclic heterocycle, optionally further having another heteroatom selected from oxygen, sulfur and nitrogen and being optionally substituted with one or more alkyl, —COalk, —COOalk, —CO—NHalk, —CS—NHalk, oxo, hydroxyalkyl, -alk-O-alk or —CO—NH$_2$ radicals, $R_{11}$ represents an alkyl, Ar or Het radical, Ar represents a phenyl, naphthyl or indenyl radical, these radicals being optionally substituted with one or more halogen atoms or alkyl, alkoxy, cyano, —CO-alk, —COOH, —COOalk, —CONR$_{12}$R$_{13}$, —CO—NH—NR$_{14}$R$_{15}$, alkylsulfanyl, alkylsulfinyl, alkylsulfonyl, -alk-NR$_{14}$R$_{15}$, —NR$_{14}$R$_{15}$, alkylthioalkyl, formyl, hydroxyl, hydroxyalkyl, —O-alk-NH-cycloalkyl, OCF$_3$, CF$_3$, —NH—CO-alk, —SO$_2$NH$_2$, —NH—COCH$_3$, —NH—COOalk or Het radicals, or alternatively, a fused ring containing a 3–10 membered Het radical is formed on 2 adjacent carbon atoms of said Ar radical, with a dioxymethylene, said Het being an unsaturated or saturated mono- or bicyclic heterocycle having one or more heteroatoms selected from oxygen, sulfur and nitrogen optionally substituted with one or more halogen atoms or alkyl, alkoxy, vinyl, alkoxycarbonyl, oxo, hydroxyl, OCF$_3$ or CF$_3$ radicals, the heterocycles that have nitrogen being optionally in their N-oxidized form;

$R_{12}$ and $R_{13}$, which are identical or different, represent a hydrogen atom or an alkyl radical or alternatively $R_{12}$ and $R_{13}$ together with the nitrogen atom to which they are attached form a 3- to 10-membered saturated mono- or bicyclic heterocycle, optionally further having another heteroatom selected from oxygen, sulfur and nitrogen and being optionally substituted with one or more alkyl radicals;

$R_{14}$ and $R_{15}$, which are identical or different, represent a hydrogen atom or an alkyl, —COOalk, cycloalkyl, alkylcycloalkyl, -alk-O-alk or hydroxyalkyl radical or alternatively $R_{14}$ and $R_{15}$ together with the nitrogen atom to which they are attached form a 3- to 10-membered saturated or unsaturated mono- or bicyclic heterocycle, optionally further having another heteroatom selected from oxygen, sulfur and nitrogen and being optionally substituted with one or more alkyl, —COalk, —COOalk, —CO—NHalk, —CS—NHalk, oxo, hydroxyalkyl, -alk-O-alk or —CO—NH$_2$ radicals, alk represents an alkyl or alkylene radical, the alkyl and alkylene radicals and portions and the alkoxy radicals and portions are in the form of a straight or branched chain having 1 to 6 carbon atoms and the cycloalkyl radicals have 3 to 10 carbon atoms, or the optical isomers thereof or pharmaceutically acceptable salts of such compound, with the exception of any compound in which $R_2$ and $R_3$ represent phenyl radicals, $R_1$ represents a radical —N(R$_5$)—Y—R$_6$, Y is SO$_2$, $R_5$ represents a methyl radical and $R_6$ represents a phenyl radical.

2. A compound according to claim 1 wherein, in formula (I), Het represents a heterocycle selected from benzimidazole, benzoxazole, benzothiazole, benzothiophene, cinnoline, thiophene, quinazoline, quinoxaline, quinoline, pyrazole, pyrrole, pyridine, imidazole, indole, isoquinoline, pyrimidine, thiazole, thiadiazole, piperidine, piperazine, pyrrolidine, triazole, furan, tetrahydroisoquinoline, tetrahydroquinoline, said heterocycle being optionally substituted with one or more halogen atoms or alkyl, alkoxy, vinyl, alkoxycarbonyl, oxo, hydroxyl, OCF$_3$ or CF$_3$ radicals.

3. A compound according to claim 1 wherein, in formula (I), $R_1$ represents a radical —N(R$_5$)—Y—R$_6$;

Y is SO$_2$;

$R_2$ represents either a phenyl which is unsubstituted or substituted with one or more halogen atoms or alkyl, alkoxy, trifluoromethyl, trifluoromethoxy, cyano, —CONR$_7$R$_8$, hydroxyalkyl or -alk-NR$_7$R$_8$ radicals; or a heteroaromatic radical selected from pyridyl, pyrimidyl, thiazolyl and thienyl rings, it being possible for these heteroaromatic radicals to be unsubstituted or substituted with a halogen atom or an alkyl, alkoxy, hydroxyl, trifluoromethyl, trifluoromethoxy, —CONR$_7$R$_8$, -alk-NR$_9$R$_{10}$, alkylsulfanyl, alkylsulfinyl, alkylsulfonyl or hydroxyalkyl radical;

$R_3$ represents either a phenyl which is unsubstituted or substituted with one or more halogen atoms or alkyl, alkoxy, trifluoromethyl, trifluoromethoxy, cyano, —CONR$_7$R$_8$, hydroxyalkyl or -alk-NR$_7$R$_8$ radicals; or a heteroaromatic radical selected from pyridyl, pyrimidyl, thiazolyl and thienyl rings, it being possible for these heteroaromatic radicals to be unsubstituted or substituted with a halogen atom or an alkyl, alkoxy, hydroxyl, trifluoromethyl, trifluoromethoxy, —CONR$_7$R$_8$, -alk-NR$_9$R$_{10}$, alkylsulfanyl, alkylsulfinyl, alkylsulfonyl or hydroxyalkyl radical, $R_5$ represents a hydrogen atom or an alkyl radical, $R_6$ represents a naphthyl, phenylalkyl, Het or phenyl radical optionally substituted with one or more halogen atoms or alkyl, alkoxy, cyano, —CO-alk, COOalk, —CONR$_{12}$R$_{13}$, -alk-NR$_{14}$R$_{15}$, —NR$_{14}$R$_{15}$, hydroxyl, hydroxyalkyl, Het, OCF$_3$, CF$_3$, —NH—CO-alk, —SO$_2$NH$_2$ or —NH—COOalk radicals, or alternatively, a fused ring containing a 3–10 membered Het radical is formed on 2 adjacent carbon atoms of said phenyl radical, with dioxymethylene, $R_7$ and $R_8$, which are identical or different, represent a hydrogen atom or an alkyl radical or alternatively $R_7$ and $R_8$ together with the nitrogen atom to which they are attached form a 3- to 10-membered saturated mono- or bicyclic heterocycle, optionally further having another heteroatom selected from oxygen, sulfur and nitrogen and being optionally substituted with one or more alkyl radicals, $R_9$ and $R_{10}$, which are identical or different, represent a hydrogen atom or an alkyl, cycloalkyl, alkylcycloalkyl or hydroxyalkyl radical or alternatively $R_9$ and $R_{10}$ together with the nitrogen atom to which they are attached form a 3- to 10-membered saturated or unsaturated mono- or bicyclic heterocycle, optionally further having another heteroatom selected from oxygen, sulfur and nitrogen and being optionally substituted with one or more alkyl, oxo or —CO—NH$_2$ radicals, $R_{12}$ and $R_{13}$, which are identical or different, represent a hydrogen atom or an alkyl radical or alternatively $R_{12}$ and $R_{13}$ together with the nitrogen atom to which they are attached form a 3- to 10-membered saturated mono- or bicyclic heterocycle, optionally further having another heteroatom selected from oxygen, sulfur and nitrogen and being optionally substituted with one or more alkyl radicals;

$R_{14}$ and $R_{15}$, which are identical or different, represent a hydrogen atom or an alkyl, cycloalkyl, alkylcycloalkyl or hydroxyalkyl radical or alternatively $R_{14}$ and $R_{15}$ together with the nitrogen atom to which they are attached form a 3- to 10-membered saturated or unsaturated mono- or bicyclic heterocycle, optionally further having another heteroatom selected from oxygen, sulfur and nitrogen and being optionally substituted with one or more alkyl, oxo, hydroxyalkyl or —CO—$NH_2$ radicals, Het represents a 3- to 10-membered unsaturated or saturated mono- or bicyclic heterocycle having one or more heteroatoms selected from oxygen, sulfur and nitrogen optionally substituted with one or more halogen atoms or alkyl, alkoxy, vinyl, alkoxycarbonyl, oxo or hydroxyl radicals, the nitrogen-containing heterocycles being optionally in their N-oxidized form, or the optical isomers thereof or pharmaceutically acceptable salts of such compound, with the exception of any compound for which $R_2$ and $R_3$ represent phenyl radicals, $R_1$ represents a radical —$N(R_5)$—Y—$R_6$, Y is $SO_2$, $R_5$ represents a methyl radical and $R_6$ represents a phenyl radical.

4. A compound according to claim 2 wherein, in formula (I), Het represents a heterocycle selected from benzimidazole, benzoxazole, benzothiazole, benzothiophene, thiophene, quinazoline, quinoxaline, quinoline, pyrrole, pyridine, imidazole, indole, isoquinoline, pyrimidine, thiazole, thiadiazole, furan, tetrahydroisoquinoline and tetrahydroquinoline, these heterocycles being optionally substituted with one or more halogen atoms or alkyl, alkoxy, vinyl, oxo, hydroxyl, $OCF_3$ or $CF_3$ radicals.

5. A compound according to claim 1 wherein, in formula (I), $R_1$ represents a radical —$N(R_5)$—Y—$R_6$;

Y is $SO_2$;

$R_2$ represents either a phenyl which is unsubstituted or substituted with one or more halogen atoms or alkyl, alkoxy, trifluoromethyl, trifluoromethoxy or hydroxyalkyl radicals; or a heteroaromatic radical selected from pyridyl and pyrimidyl rings, it being possible for these heteroaromatic radicals to be unsubstituted or substituted with a halogen atom or an alkyl, alkoxy, hydroxyl, trifluoromethyl or trifluoromethoxy radical;

$R_3$ represents either a phenyl which is unsubstituted or substituted with one or more halogen atoms or alkyl, alkoxy, trifluoromethyl, trifluoromethoxy or hydroxyalkyl radicals; or a heteroaromatic radical selected from pyridyl and pyrimidyl rings, it being possible for these heteroaromatic radicals to be unsubstituted or substituted with a halogen atom or an alkyl, alkoxy, hydroxyl, trifluoromethyl or trifluoromethoxy radical, $R_5$ represents a hydrogen atom or an alkyl radical, $R_6$ represents a naphthyl, phenylalkyl, Het or phenyl radical optionally substituted with one or more halogen atoms or alkyl, alkoxy, —$NR_{14}R_{15}$, hydroxyl, hydroxyalkyl, $OCF_3$, $CF_3$ or —$SO_2NH_2$ radicals, or alternatively, a fused ring containing a 3–10 membered Het radical is formed on 2 adjacent carbon atoms of said phenyl radical, with dioxymethylene, $R_{14}$ and $R_{15}$, which are identical or different, represent a hydrogen atom or an alkyl, cycloalkyl, alkylcycloalkyl or hydroxyalkyl radical or alternatively $R_{14}$ and $R_{15}$ together with the nitrogen atom to which they are attached form a 3- to 10-membered saturated or unsaturated mono- or bicyclic heterocycle, optionally further having another heteroatom selected from oxygen, sulfur and nitrogen and being optionally substituted with one or more alkyl, oxo, hydroxyalkyl or —CO—$NH_2$ radicals, Het represents a 3- to 10-membered unsaturated or saturated mono- or bicyclic heterocycle containing one or more heteroatoms selected from oxygen, sulfur and nitrogen optionally substituted with one or more halogen atoms or alkyl, alkoxy, vinyl, alkoxycarbonyl, oxo or hydroxyl radicals, the heterocycles that have nitrogen being optionally in their N-oxidized form, or the optical isomers thereof or pharmaceutically acceptable salts of such compound, with the exception of any compound in which $R_2$ and $R_3$ represent phenyl radicals, $R_1$ represents a radical —$N(R_5)$—Y—$R_6$, Y is $SO_2$, $R_5$ represents a methyl radical and $R_6$ represents a phenyl radical.

6. A compound according to claim 5 wherein, in formula (I), Het represents a heterocycle selected from benzimidazole, benzoxazole, benzothiazole, benzothiophene, thiophene, quinoline, pyrrole, pyridine, pyrimidine, thiazole, thiadiazole, furan, tetrahydroisoquinoline and tetrahydroquinoline, these heterocycles being optionally substituted with one or more halogen atoms or alkyl, alkoxy, vinyl, oxo, hydroxyl, $OCF_3$ or $CF_3$ radicals.

7. A process for preparing a compound of formula (I) according to claim 1 in which $R_1$ represents a radical —$NHCOR_4$, the process comprising reacting an acid $R_4COOH$ for which $R_4$ has the same meanings as in claim 1 with a derivative of formula:

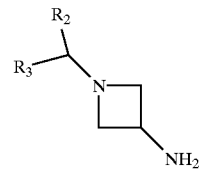

in which $R_2$ and $R_3$ have the same meanings as in claim 1, isolating the product, and optionally converting the product to a pharmaceutically acceptable salt.

8. A process for preparing a compound of formula (I) according to claim 1 in which $R_1$ represents a radical —$N(R_5)$—Y—$R_6$, the process comprising reacting a derivative of formula:

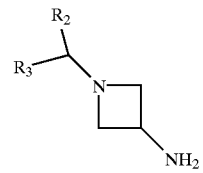

which $R_2$ and $R_3$ have the same meanings as in claim 1 with a derivative Hal-Y—$R_6$ in which Y and $R_6$ have the same meanings as in claim 1 and Hal represents a halogen atom, optionally followed by reacting the product with a derivative Hal-alk, in which Hal represents a halogen atom and alk represents a C1–6 straight or branched chain alkyl radical to produce the compounds in which $R_5$ is an alkyl radical, isolating the product, and optionally converting the product to a pharmaceutically acceptable salt.

9. A process for preparing a compound of formula (I) according to claim 1, the process comprising reacting a derivative $R_2$—CHBr—$R_3$ in which $R_2$ and $R_3$ have the same meanings as in claim 1 with a derivative of formula:

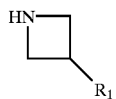

in which $R_1$ has the same meanings as in claim 1, isolating the product, and optionally converting the product to a pharmaceutically acceptable salt.

10. A process for preparing a compound of formula (I) according to claim 1 in which $R_1$ represents a radical —N($R_5$)—Y—$R_6$ in which $R_6$ is a phenyl radical substituted with a hydroxyl radical, the process comprising hydrolyzing a corresponding compound of formula (I) in which $R_1$ represents a radical —N($R_5$)—Y—$R_6$ in which $R_6$ is a phenyl radical substituted with an alkoxy radical, isolating the product, and optionally converting the product to a pharmaceutically acceptable salt.

11. A process for preparing a compound of formula (I) according to claim 1 in which $R_1$ represents a radical —N($R_5$)—Y—$R_6$ in which $R_6$ is a phenyl radical substituted with a hydroxy(1C)alkyl radical, the process comprising reacting diisobutylaluminum hydride with a corresponding compound of formula (I) in which $R_1$ represents a radical —N($R_5$)—Y—$R_6$ in which $R_6$ is a phenyl radical substituted with an alkoxycarbonyl radical, isolating the product, and optionally converting the product to a pharmaceutically acceptable salt.

12. A process for preparing a compound of formula (I) according to claim 1 in which $R_1$ represents a radical —N($R_5$)—Y—$R_6$ in which $R_6$ is a phenyl radical substituted with a 1-pyrrolidinyl radical, the process comprising reacting pyrrolidine with a corresponding compound of formula (I) in which $R_1$ represents a radical —N($R_5$)—Y—$R_6$ in which $R_6$ is a phenyl radical substituted with a fluorine atom, isolating the product, and optionally converting the product to a pharmaceutically acceptable salt.

13. A pharmaceutical composition comprising, as an active ingredient, a compound of formula:

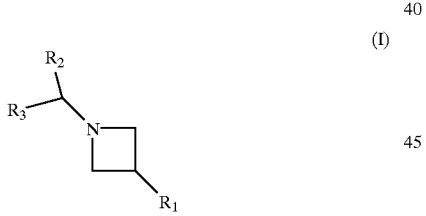

(I)

in which
$R_1$ represents a radical —NHCOR$_4$ or —N($R_5$)—Y—$R_6$, Y is CO or SO$_2$, $R_2$ and $R_3$, which are identical or different, represent either an aromatic radical selected from phenyl, naphthyl and indenyl, these aromatic radicals being unsubstituted or substituted with one or more halogen atoms or alkyl, alkoxy, formyl, hydroxyl, trifluoromethyl, trifluoro-methoxy, —CO-alk, cyano, —COOH, —COOalk, —CONR$_7$R$_8$, —CO—NH—NR$_9$R$_{10}$, alkylsulfanyl, alkylsulfinyl, alkyl-sulfonyl, alkylsulfanylalkyl, alkylsulfinylalkyl, alkylsulfonylalkyl, hydroxyalkyl or -alk-NR$_7$R$_8$ radicals; or a heteroaromatic radical selected from benzofuryl, benzothiazolyl, benzothienyl, benzoxazolyl, chromanyl, 2,3-dihydrobenzofuryl, 2,3-dihydrobenzothienyl, pyrimidinyl, furyl, imidazolyl, isochromanyl, isoquinolyl, pyrrolyl, pyridyl, quinolyl, 1,2,3,4-tetrahydroisoquinolyl, thiazolyl and thienyl rings, these heteroaromatic radicals being unsubstituted or substituted with a halogen atom or an alkyl, alkoxy, hydroxyl, trifluoromethyl, trifluoromethoxy, cyano, —COOH, —COOalk, —CO—NH—NR$_9$R$_{10}$, —CONR$_7$R$_8$, -alk-NR$_9$R$_{10}$, alkylsulfanyl, alkylsulfinyl, alkylsulfonyl, alkylsulfanylalkyl, alkylsulfinylalkyl, alkylsulfonylalkyl or hydroxyalkyl radical, $R_4$ represents a radical selected from -alk-SO$_2$—R$_{11}$, -alk-SO$_2$—CH═CH—R$_{11}$, Het substituted with —SO$_2$—R$_{11}$ and phenyl substituted with —SO$_2$—R$_{11}$ or -alk-SO$_2$—R$_{11}$, $R_5$ represents a hydrogen atom or an alkyl radical, $R_6$ represents a phenylalkyl, Het or Ar radical, $R_7$ and $R_8$, which are identical or different, represent a hydrogen atom or an alkyl radical or, alternatively, $R_7$ and $R_8$ form, together with the nitrogen atom to which they are attached, a 3- to 10-membered saturated mono- or bicyclic heterocycle, optionally containing another heteroatom selected from oxygen, sulfur and nitrogen and being optionally substituted with one or more alkyl radicals, $R_9$ and $R_{10}$, which are identical or different, represent a hydrogen atom or an alkyl, —COOalk, cycloalkyl, alkylcycloalkyl, -alk-O-alk or hydroxyalkyl radical or, alternatively, $R_9$ and $R_{10}$ form, together with the nitrogen atom to which they are attached, a 3- to 10-membered saturated or unsaturated mono- or bicyclic heterocycle, said heterocycle optionally containing another heteroatom selected from oxygen, sulfur and nitrogen and being optionally substituted with one or more alkyl, —COalk, —COOalk, —CO—NHalk, —CS—NHalk, oxo, hydroxyalkyl, -alk-O-alk or —CO—NH$_2$ radicals, $R_{11}$ represents an alkyl, Ar or Het radical, Ar represents a phenyl, naphthyl or indenyl radical, these radicals being optionally substituted with one or more halogen atoms or alkyl, alkoxy, cyano, —CO-alk, —COOH, —COOalk, —CONR$_{12}$R$_{13}$, —CO—NH—NR$_{14}$R$_{15}$, alkylsulfanyl, alkylsulfinyl, alkylsulfonyl, -alk-NR$_{14}$R$_{15}$, —NR$_{14}$R$_{15}$, alkylthioalkyl, formyl, hydroxyl, hydroxyalkyl, —O-alk-NH-cycloalkyl, OCF$_3$, CF$_3$, —NH—CO-alk, —SO$_2$NH$_2$, —NH—COCH$_3$, —NH—COOalk or Het radicals or, alternatively, a fused ring containing a 3–10 membered Het radical is formed on 2 adjacent carbon atoms of said Ar radical, with a dioxymethylene, said Het being an unsaturated or saturated mono- or bicyclic heterocycle containing one or more heteroatoms selected from oxygen, sulfur and nitrogen optionally substituted with one or more halogen atoms or alkyl, alkoxy, vinyl, alkoxycarbonyl, oxo, hydroxyl, OCF$_3$ or CF$_3$ radicals, the nitrogen-containing heterocycles being optionally in their N-oxidized form, $R_{12}$ and $R_{13}$, which are identical or different, represent a hydrogen atom or an alkyl radical or alternatively $R_{12}$ and $R_{13}$ together form with the nitrogen atom to which they are attached a 3- to 10-membered saturated mono- or bicyclic heterocycle, optionally containing another heteroatom selected from oxygen, sulfur and nitrogen and being optionally substituted with one or more alkyl radicals, $R_{14}$ and $R_{15}$, which are identical or different, represent a hydrogen atom or an alkyl, —COOalk, cycloalkyl, alkylcycloalkyl, -alk-O-alk or hydroxyalkyl radical or alternatively $R_{14}$ and $R_{15}$ together form with the nitrogen atom to which they are attached a 3- to 10-membered saturated or unsaturated mono- or bicyclic heterocycle, optionally containing another heteroatom selected from oxygen, sulfur and nitrogen and being optionally substituted with one or more alkyl, —COalk, —COOalk, —CO—NHalk, —CS—NHalk, oxo, hydroxyalkyl, -alk-O-alk or —CO—NH$_2$ radicals, alk represents an alkyl or alkylene radical, the alkyl and alkylene radicals and portions and the alkoxy radicals and portions are in the form of a straight or branched chain and contain 1 to 6 carbon atoms and the cycloalkyl radicals contain 3 to 10 carbon atoms, an optical isomer of such a compound or one of its pharmaceutically acceptable salts.

14. A pharmaceutical composition according to claim 13 wherein, in the compound of formula (I), Het represents a heterocycle selected from benzimidazole, benzoxazole, benzothiazole, benzothiophene, cinnoline, thiophene, quinazoline, quinoxaline, quinoline, pyrazole, pyrrole, pyridine, imidazole, indole, isoquinoline, pyrimidine, thiazole, thiadiazole, piperidine, piperazine, pyrrolidine, triazole, furan, tetrahydroisoquinoline, tetrahydroquinoline, said heterocycle being optionally substituted with one or more halogen atoms or alkyl, alkoxy, vinyl, alkoxycarbonyl, oxo, hydroxyl, OCF$_3$ or CF$_3$ radicals.

15. A pharmaceutical composition according to claim 13 comprising, as an active ingredient, at least one compound of formula (I) wherein $R_1$ represents a radical —N($R_5$)—Y—$R_6$, Y is SO$_2$, $R_2$ represents either a phenyl which is unsubstituted or substituted with one or more halogen atoms or alkyl, alkoxy, trifluoromethyl, trifluoromethoxy, cyano, —CONR$_7$R$_8$, hydroxyalkyl or -alk-NR$_7$R$_8$ radicals; or a heteroaromatic radical selected from pyridyl, pyrimidyl, thiazolyl and thienyl rings, it being possible for these heteroaromatic radicals to be unsubstituted or substituted with a halogen atom or an alkyl, alkoxy, hydroxyl, trifluoromethyl, trifluoromethoxy, —CONR$_7$R$_8$, -alk-NR$_9$R$_{10}$, alkylsulfanyl, alkylsulfinyl, alkylsulfonyl or hydroxyalkyl radical, $R_3$ represents either a phenyl which is unsubstituted or substituted with one or more halogen atoms or alkyl, alkoxy, trifluoromethyl, trifluoromethoxy, cyano, —CONR$_7$R$_8$, hydroxyalkyl or -alk-NR$_7$R$_8$ radicals; or a heteroaromatic radical selected from pyridyl, pyrimidyl, thiazolyl and thienyl rings, it being possible for these heteroaromatic radicals to be unsubstituted or substituted with a halogen atom or an alkyl, alkoxy, hydroxyl, trifluoromethyl, trifluoromethoxy, —CONR$_7$R$_8$, -alk-NR$_9$R$_{10}$, alkylsulfanyl, alkylsulfinyl, alkylsulfonyl or hydroxyalkyl radical, $R_5$ represents a hydrogen atom or an alkyl radical, $R_6$ represents a naphthyl, phenylalkyl, Het or phenyl radical optionally substituted with one or more halogen atoms or alkyl, alkoxy, cyano, —CO-alk, COOalk, —CONR$_{12}$R$_{13}$, -alk-NR$_{14}$R$_{15}$, —NR$_{14}$R$_{15}$, hydroxyl, hydroxyalkyl, Het, OCF$_3$, CF$_3$, —NH—CO-alk, —SO$_2$NH$_2$ or —NH—COOalk radicals, or alternatively, a fused ring containing a 3–10 membered Het radical is formed on 2 adjacent carbon atoms of said phenyl radical, with dioxymethylene, $R_7$ and $R_8$, which are identical or different, represent a hydrogen atom or an alkyl radical or alternatively $R_7$ and $R_8$ together form with the nitrogen atom to which they are attached a 3- to 10-membered saturated mono- or bicyclic heterocycle, optionally containing another heteroatom selected from oxygen, sulfur and nitrogen and being optionally substituted with one or more alkyl radicals, $R_9$ and $R_{10}$, which are identical or different, represent a hydrogen atom or an alkyl, cycloalkyl, alkylcycloalkyl or hydroxyalkyl radical or alternatively $R_9$ and $R_{10}$ together form with the nitrogen atom to which they are attached a 3- to 10-membered saturated or unsaturated mono- or bicyclic heterocycle, optionally containing another heteroatom selected from oxygen, sulfur and nitrogen and being optionally substituted with one or more alkyl, oxo or —CO—NH$_2$ radicals, $R_{12}$ and $R_{13}$, which are identical or different, represent a hydrogen atom or an alkyl radical or alternatively $R_{12}$ and $R_{13}$ together form with the nitrogen atom to which they are attached a 3- to 10-membered saturated mono- or bicyclic heterocycle, optionally containing another heteroatom selected from oxygen, sulfur and nitrogen and being optionally substituted with one or more alkyl radicals, $R_{14}$ and $R_{15}$, which are identical or different, represent a hydrogen atom or an alkyl, cycloalkyl, alkylcycloalkyl or hydroxyalkyl radical or alternatively $R_{14}$ and $R_{15}$ together form with the nitrogen atom to which they are attached a 3- to 10-membered saturated or unsaturated mono- or bicyclic heterocycle, optionally containing another heteroatom selected from oxygen, sulfur and nitrogen and being optionally substituted with one or more substituents selected from alkyl, oxo, hydroxyalkyl and —CO—NH$_2$ radicals, Het represents a 3- to 10-membered unsaturated or saturated mono- or bicyclic heterocycle containing one or more heteroatoms selected from oxygen, sulfur and nitrogen optionally substituted with one or more halogen atoms or alkyl, alkoxy, vinyl, alkoxycarbonyl, oxo or hydroxyl radicals, the nitrogen-containing heterocycles being optionally in their N-oxidized form, an optical isomer of such a compound or one of its pharmaceutically acceptable salts.

16. A pharmaceutical composition according to claim 15 wherein, in the compound of formula (I), Het represents a heterocycle selected from benzimidazole, benzoxazole, benzothiazole, benzothiophene, thiophene, quinazoline, quinoxaline, quinoline, pyrrole, pyridine, imidazole, indole, isoquinoline, pyrimidine, thiazole, thiadiazole, furan, tetrahydroisoquinoline and tetrahydroquinoline, these heterocycles being optionally substituted with one or more substituents selected from halogen, alkyl, alkoxy, vinyl, oxo, hydroxyl, OCF$_3$ and CF$_3$ radicals.

17. A pharmaceutical composition according to claim 13 comprising, as an active ingredient, at least one compound of formula (I) wherein $R_1$ represents a radical —N($R_5$)—Y—$R_6$, Y is SO$_2$, $R_2$ represents either a phenyl which is unsubstituted or substituted with one or more halogen atoms or alkyl, alkoxy, trifluoromethyl, trifluoromethoxy or hydroxyalkyl radicals; or a heteroaromatic radical selected from pyridyl and pyrimidyl rings, it being possible for these heteroaromatic radicals to be unsubstituted or substituted with a halogen atom or an alkyl, alkoxy, hydroxyl, trifluoromethyl or trifluoromethoxy radical, $R_3$ represents either a phenyl which is unsubstituted or substituted with one or more halogen atoms or alkyl, alkoxy, trifluoromethyl, trifluoromethoxy or hydroxyalkyl radicals; or a heteroaromatic radical selected from pyridyl and pyrimidyl rings, it being possible for these heteroaromatic radicals to be unsubstituted or substituted with a halogen atom or an alkyl, alkoxy, hydroxyl, trifluoromethyl or trifluoromethoxy radical, $R_5$ represents a hydrogen atom or an alkyl radical, $R_6$ represents a naphthyl, phenylalkyl, Het or phenyl radical optionally substituted with one or more halogen atoms or alkyl, alkoxy, —$NR_{14}R_{15}$, hydroxyl, hydroxyalkyl, $OCF_3$, $CF_3$ or —$SO_2NH_2$ radicals, or alternatively, a fused ring containing a 3–10 membered Het radical is formed on 2 adjacent carbon atoms of said phenyl radical, with dioxymethylene, $R_{14}$ and $R_{15}$, which are identical or different, represent a hydrogen atom or an alkyl, cycloalkyl, alkylcycloalkyl or hydroxyalkyl radical or alternatively $R_{14}$ and $R_{15}$ together with the nitrogen atom to which they are attached form a 3- to 10-membered saturated or unsaturated mono- or bicyclic heterocycle, optionally containing another heteroatom selected from oxygen, sulfur and nitrogen and being optionally substituted with one or more alkyl, oxo, hydroxyalkyl or —CO—$NH_2$ radicals, Het represents a 3- to 10-membered unsaturated or saturated mono- or bicyclic heterocycle containing one or more heteroatoms selected from oxygen, sulfur and nitrogen optionally substituted with one or more halogen atoms or alkyl, alkoxy, vinyl, alkoxycarbonyl, oxo or hydroxyl radicals, the nitrogen-containing heterocycles being optionally in their N-oxidized form, an optical isomer of such a compound or one of its pharmaceutically acceptable salts.

18. A pharmaceutical composition according to claim 17 wherein, in the compound of formula (I), Het represents a heterocycle selected from benzimidazole, benzoxazole, benzothiazole, benzothiophene, thiophene, quinoline, pyrrole, pyridine, pyrimidine, thiazole, thiadiazole, furan, tetrahydroisoquinoline and tetrahydroquinoline, these heterocycles being optionally substituted with one or more halogen atoms or alkyl, alkoxy, vinyl, oxo, hydroxyl, $OCF_3$ or $CF_3$ radicals.

* * * * *